(12) United States Patent
Sala et al.

(10) Patent No.: US 12,700,480 B2
(45) Date of Patent: Aug. 4, 2026

(54) METHOD FOR MONITORING OR VALIDATING FRAGRANCE COMPOSITIONS

(71) Applicant: BASF SE, Ludwigshafen am Rhein (DE)

(72) Inventors: Oliver Sala, Ludwigshafen (DE); Miriam Mathea, Ludwigshafen (DE); Rebecca Sure, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 609 days.

(21) Appl. No.: 18/023,508

(22) PCT Filed: Aug. 31, 2021

(86) PCT No.: PCT/EP2021/073989
§ 371 (c)(1),
(2) Date: Feb. 27, 2023

(87) PCT Pub. No.: WO2022/043574
PCT Pub. Date: Mar. 3, 2022

(65) Prior Publication Data
US 2023/0360744 A1 Nov. 9, 2023

(30) Foreign Application Priority Data

Aug. 31, 2020 (EP) .................................... 20193571

(51) Int. Cl.
G16C 60/00 (2019.01)
A23L 27/00 (2016.01)
(Continued)

(52) U.S. Cl.
CPC ............. G16C 60/00 (2019.02); G16C 20/30 (2019.02); G16C 20/70 (2019.02); A23L 27/00 (2016.08);
(Continued)

(58) Field of Classification Search
CPC ........ G16C 60/00; G16C 20/30; G16C 20/70; C11B 9/00; A23L 27/00; G06Q 10/04; G06Q 10/10
See application file for complete search history.

(56) References Cited

U.S. PATENT DOCUMENTS 11,278,483 B2 3/2022 Lefevre et al.
2016/0376520 A1 12/2016 Absher et al.
(Continued)

FOREIGN PATENT DOCUMENTS

JP 2007285751 A 11/2007
JP 2018109099 A 7/2018
(Continued)

OTHER PUBLICATIONS

Klamt (Conductor-like Screening Model for Real Solvents: A New Approach to the Quantitative Calculation of Solvation Phenomena, The Journal of Physical Chemistry, vol. 99 No. 7, American Chemical Society, Feb. 1, 1995, doi: 10.1021/j100007a062) (Year: 1995).*
(Continued)

*Primary Examiner* — Christian T Bryant
(74) *Attorney, Agent, or Firm* — Lowenstein Sandler LLP

(57) ABSTRACT

The present invention relates to a method for generating or predicting temporal evaporation profiles of a fragrance product comprising a plurality of fragrance ingredients by determining the composition of the gas phase and/or condensed phase of the composition over time via quantum chemical calculations and displaying the temporal fragrance ingredient profile and/or the temporal odour families profile and/or any other temporal performance criteria profile (e.g. boost-retention) in order to visualize the temporal performance and olfactive perception of the fragrance product, a device for generating or predicting temporal evaporation profiles, computer program element controlling such a device and a (Continued)

10 computer readable medium having stored said computer program element.

15 Claims, 10 Drawing Sheets

(51) Int. Cl.
| | | |
|---|---|---|
| *C11B 9/00* | (2006.01) |
| *G06Q 10/04* | (2023.01) |
| *G06Q 10/10* | (2023.01) |
| *G16C 20/30* | (2019.01) |
| *G16C 20/70* | (2019.01) |

(52) U.S. Cl.
CPC ................ *C11B 9/00* (2013.01); *G06Q 10/04* (2013.01); *G06Q 10/10* (2013.01)

(56) References Cited

U.S. PATENT DOCUMENTS

| | | | | |
|---|---|---|---|---|
| 2018/0180391 A1* | 6/2018 | Holland | ................ | A61K 8/492 |
| 2018/0334637 A1* | 11/2018 | Holland | ................ | C11B 9/0019 |
| 2021/0193271 A1* | 6/2021 | Lelievre | ................ | C11B 9/00 |

FOREIGN PATENT DOCUMENTS

| | | | | |
|---|---|---|---|---|
| KR | 20160058545 A | 5/2016 | | |
| WO | WO-2017173516 A1 * | 10/2017 | ............... | F24F 8/50 |
| WO | 2019238680 A1 | 12/2019 | | |

OTHER PUBLICATIONS

Teixeira et al. (The diffusion of perfume mixtures and the odor performance, Chemical Engineering Science, vol. 64, Issue 11, 2009, pp. 2570-2589, ISSN 0009-2509, https://doi.org/10.1016/j.ces.2009.01.064) (Year: 2009).*

Friberg et al. ("Vapour Pressure of a Fragrance Ingredient during Evaporation in a Simple Emulsion." International Journal of Cosmetic Science, 1997.) (Year: 1997).*

Christine Vuilleumier et al: "Multidimensional Visualization of Physical and Perceptual Data Leading to a Creative Approach in Fragrance Development Physical Parameters of Perfumery Raw Materials", Sep. 1, 2008 (Sep. 1, 2008), pp. 1-8, XP055602161, Retrieved from the Internet: URL:https://media.allured.com/documents/PF 33 09 054 08.pdf.

International Search Report and Written Opinion for PCT/EP2021/073989 dated Dec. 9, 2021, 12 pages.

European Search Report for European Patent Application No. 20193571.5 dated Feb. 16, 2021, 9 pages.

* cited by examiner

300

300

METHOD FOR MONITORING OR VALIDATING FRAGRANCE COMPOSITIONS

CROSS-REFERENCE TO RELATED APPLICATION SECTIONS

The present application is a national stage entry under 35 U.S.C. § 371 of International Application No. PCT/EP2021/073989, filed on Aug. 31, 2021, which claims priority to European Patent Application No. 20193571.5, filed on Aug. 31, 2020, the contents of which are hereby incorporated by reference in their entirety.

FIELD OF THE INVENTION

The present invention relates to a computer-implemented method, apparatus and computer program for generating temporal evaporation profiles usable for validating and/or monitoring the fragrance product.

TECHNICAL BACKGROUND

State of the art fragrance compositions are prepared from a palette of different fragrance ingredients which are known for their different olfactive characters. When creating a fragrance the perfumer selects ingredients and combines them based on their olfactive character and their relative proportions. This process is usually guided by the experience of the perfumer which allows her or him to form a reasonable mental impression of the odour of the composition.

WO 2019/238680 A1 discloses a computer-implemented method for predicting the temporal fragrance profile of a fragrance composition, which is based on retrieving a diffusion measure of how fast each fragrance ingredient diffuses into a headspace.

SUMMARY OF THE INVENTION

There is a need to improve the generation of the temporal evaporation profiles of a fragrance product comprising a fragrance composition and a matrix in order to provide a more reliable process for producing fragrance products.

In one aspect disclosed herein is a computer-implemented method for generating a temporal evaporation profile of a fragrance product comprising a fragrance composition and a matrix, wherein the fragrance composition comprises one or a plurality of fragrance ingredient(s), comprising the steps of:

a) receiving or obtaining fragrance composition data associated with one or more fragrance ingredients of the fragrance composition and matrix data associated with the matrix;

b) providing a vapour pressure of each fragrance ingredient based on the fragrance ingredients data;

c) determining, based on the fragrance ingredients data and the matrix data, a time-dependent interaction coefficient of each fragrance ingredient in a condensed phase of the fragrance composition in the matrix over a predetermined period of time;

d) generating, based on the provided vapour pressure and the determined time-dependent interaction coefficient, the temporal evaporation profile of the fragrance product, wherein the temporal evaporation profile is related to a time-dependent quantity associated with the evaporation behaviour of each fragrance ingredient of the fragrance product over the predetermined period of time; and e) providing the generated temporal evaporation profile preferably usable for validating and/or monitoring the fragrance product or composition with respect to one or more performance characteristic(s).

In another aspect disclosed herein is a computer-implemented method for monitoring and/or validating production of a fragrance product, the method comprising the steps of:

receiving the temporal evaporation profile as generated according to any of the methods disclosed herein, monitoring and/or validating the fragrance product based on the temporal evaporation profile.

In another aspect disclosed herein is a computer-implemented method for monitoring production of a fragrance product, the method comprising the steps of:

receiving the temporal evaporation profile as generated according to any of the methods disclosed herein, wherein the temporal evaporation profile is indicative of quality criteria, measuring one or more performance characteristic(s) of the produced fragrance product, determining, based on the temporal evaporation profile and the performance characteristic, if the produced fragrance product fulfils quality criteria.

In another aspect disclosed herein is a computer-implemented method for validating production of a fragrance product, the method comprising the steps of:

receiving an existing temporal evaporation profile as generated according to any of the methods disclosed herein based on existing fragrance data associated with existing fragrance ingredients and matrix data associated with existing matrix component(s), wherein the existing temporal evaporation profile is indicative of quality criteria, receiving precursor data and generating a new temporal evaporation profile according to any of the methods disclosed herein based on the precursor data, determining, based on the existing temporal evaporation profile and the new temporal evaporation profile, if the precursor(s) fulfils quality criteria.

In another aspect disclosed herein is an apparatus for generating a temporal evaporation profile of a fragrance product comprising a fragrance composition and a matrix, wherein the fragrance composition comprises one or a plurality of fragrance ingredient(s), the apparatus comprising one or more processing unit(s) configured to generate a temporal evaporation profile of the fragrance product, wherein the processing unit(s) include instructions, which when executed on the one or more processing unit(s) perform the following steps:

a) receiving or obtaining fragrance composition data associated with one or more fragrance ingredients of the fragrance composition and matrix data associated with the matrix;

b) providing a vapour pressure of each fragrance ingredient based on the fragrance ingredients data;

c) determining, based on the fragrance ingredients data and the matrix data, a time-dependent interaction coefficient of each fragrance ingredient in a condensed phase of the fragrance composition in the matrix over a predetermined period of time;

d) generating, based on the provided vapour pressure and the determined time-dependent interaction coefficient, the temporal evaporation profile of the fragrance product, wherein the temporal evaporation profile is related to a time-dependent quantity associated with the evaporation behaviour of each fragrance ingredient of the fragrance product over the predetermined period of time; and e) providing the generated temporal evaporation profile preferably usable for validating and/or monitoring the fragrance product or composition with respect to a performance characteristic.

In another aspect disclosed herein is an apparatus for monitoring and/or validating production of a fragrance product, the apparatus comprising one or more processing unit(s) configured to monitor and/or validate production, wherein the processing unit(s) include instructions, which when executed on the one or more processing unit(s) perform the following steps:

receiving the temporal evaporation profile as generated according to any of the methods disclosed herein, monitoring and/or validating the fragrance product based on the temporal evaporation profile.

In another aspect disclosed herein is an apparatus for monitoring production of a fragrance product, the apparatus comprising one or more processing unit(s) configured to monitor production, wherein the processing unit(s) include instructions, which when executed on the one or more processing unit(s) perform the following steps:

receiving the temporal evaporation profile as generated according to any of the methods disclosed herein, wherein the temporal evaporation profile is indicative of quality criteria, measuring a performance characteristic of the produced fragrance product, determining, based on the temporal evaporation profile and the performance characteristic, if the produced fragrance product fulfils quality criteria.

In another aspect disclosed herein is an apparatus for validating production of a fragrance product, the apparatus comprising one or more processing unit(s) configured to validate production of a fragrance product, wherein the processing unit(s) include instructions, which when executed on the one or more processing unit(s) perform the following steps:

receiving an existing temporal evaporation profile as generated according to any of the methods disclosed herein, preferably based on existing fragrance data associated with existing fragrance ingredients and matrix data associated with existing matrix component (s), wherein the existing temporal evaporation profile is indicative of quality criteria, receiving precursor data and generating a temporal evaporation profile according to any of the methods disclosed herein based on the precursor data, determining, based on the existing temporal evaporation profile and the new temporal evaporation profile, if the precursor(s) fulfils quality criteria.

According to another aspect of the present invention, there is provided a computer-implemented method for predicting or generating a temporal evaporation profile of a fragrance composition in a matrix comprising a plurality of fragrance ingredients, comprising the steps of:

a) receiving a user input or fragrance composition data that defines the fragrance ingredients of the fragrance composition and matrix data that defines the matrix;

b) optionally determining a molecular geometry of each fragrance ingredient, which may depend on the matrix;

c) providing a vapour pressure of each fragrance ingredient or determining a vapour pressure of each fragrance ingredient based on the respective determined molecular geometry;

d) determining a time-dependent interaction coefficient of each fragrance ingredient in a condensed phase of the fragrance composition in the matrix over a predetermined period of time;

e) determining, based on the determined vapour pressure and the determined time-dependent interaction coefficient, the temporal evaporation profile of the fragrance composition in the matrix, wherein the temporal evaporation profile comprises a time-dependent quantity associated with the evaporation behaviour or a time-dependent fractural amount of each fragrance ingredient in a gas phase and/or the condensed phase of the fragrance composition in the matrix over the predetermined period of time; and f) providing the determined temporal evaporation profile, which is usable for validating the fragrance composition in the matrix with respect to a performance characteristic.

By determining the time dependent interaction coefficients of each fragrance ingredient, the dynamic behavior of the fragrance product including the interactions between different fragrance ingredients and/or between fragrance ingredient(s) and the matrix are considered in generating the temporal evaporation profile. This way the main chemical and/or physical characteristics determining the odor of the fragrance product can be determined in a dynamic way considering correlations in a time-dependent manner. Such dynamic behavior impacts the condensed phase in such a way that the temporal evaporation profile changes.

The methods for generating or predicting temporal odour profiles or temporal evaporation profiles of a fragrance composition or product may be based on quantum chemical calculations, which include the chemical interactions of the matrix and allow predictions of the chemical and olfactory behaviour of new fragrance ingredients or new matrices. The method thus provides a beneficial production aid which allows adaptations of fragrance compositions to different applications or identification of possible malodours by broadening the spectrum of objectively determining olfactive characters of fragrance ingredients.

The generation of the temporal evaporation profile solves a key need in any industry concerned with odors. Odors are thus far evaluated in a subjective human based manner. Multiple humans smell the odor and give feedback. The subjective data may be to a certain extent put into objective terms by statistical methods. However, such a process can only provide a certain degree of objectivity and is limited by the data generation via human perception. The method disclosed herein overcomes this deficiency by using physical and/or chemical properties of the fragrance composition that are key factors influencing the odor of the fragrance product. This way the chemical and/or physical properties of the fragrance composition and their dynamic behavior can be quantified in an objective manner, solving an important need in the industry to make fragrance products objectively comparable and with that to monitor product quality in the production process or to control the production process to deliver the expected results with respect to the odor perception of the fragrance product.

In particular, the monitoring and/or validation of the fragrance composition is a key factor to ensure consistent quality of a fragrance product. The temporal evaporation profile of a fragrance product or composition as disclosed herein allows for monitoring and/or controlling production processes. Fragrance product production is highly sensitive to impurities that negatively impact the odor of the produced fragrance product. The generated temporal evaporation profile allows for the first time to provide objective quality or performance parameters that are based on chemical and/or physical properties of the fragrance product and can be measured in the production processes. A comparison of the measured and the generated temporal evaporation profile or quantities derived therefrom allows not only for quality control or more reliable production but may be extended via a feedback loop which adjusts the production process, where needed.

It is an object of the present invention to provide an objective measure for the odor of a fragrance composition enabling a more reliable production process for fragrance product. These and other objects, which become apparent upon the following description, are solved by the subject matter of the independent claims. The dependent claims refer to preferred embodiments of the invention.

In other words, a computer-implemented method is proposed for generating or predicting temporal evaporation profiles of a fragrance product. The proposed method considers the chemical interactions (e.g. hydrogen bonding, ionic bonding, dipole forces or van der Waals forces) of the fragrance ingredients with the matrix. Thus, it is possible to identify the difference between the temporal evaporation profile of the pure fragrance composition oil and the temporal evaporation profile of an eau de parfum or eau de toilette, which includes different amounts of ethanol. By considering these differences in chemical interactions between the fragrance ingredients and the matrix, it is also possible to determine the occurrence of malodours and/or off-odours in a specific matrix, which may not be present in other matrices.

The activity coefficient may be an interaction coefficient used in thermodynamics to account for deviations from ideal behavior in a mixture of chemical substances. Any interactions coefficient or combination of interaction coefficients accounting for such deviation may be used. The time-dependent interaction or activity coefficient of every ingredient in the mixture may be determined in the beginning and updated in certain intervals over time in step as the composition of the mixture of the condensed phase alters due to distinct evaporation of fragrant ingredients into the gas phase from the condensed phase mixture. Thus, the time-dependent interaction or activity coefficient may link with real behavior of substances in condensed phase. This may be beneficial when dealing with mixtures in which the composition changes over time e.g. due to different evaporation behavior of components. Thus, the time-dependent interaction or activity coefficient can be used to reflect the dynamic consideration of evaporation of ingredients on the time scale. In addition volume, radiance, diffusive character may be derived or added.

The determined temporal evaporation profile may represent an objective representation of a subjective measure such as olfactory perception. In this way, compositions with matrix and fragrance ingredients may be checked objectively to validate customer requirements of olfactory characteristics, to validate recipes before production/delivery and to tailor chemical products to the needs of customers. Thus, the evaluation does not rely on the subjective impact of test persons or other experimental data.

Further benefits of the proposed computer-implemented method may include one or more of the following:

The determined temporal evaporation profile may be used in scent design and production for consumer products, fine fragrances, aroma chemicals and life-style products.

The determined temporal evaporation profile may be used for precepting, monitoring, and eliminating malodours and masking bad smell.

The proposed computer-implemented method may be suitable for generating temporal evaporation profiles of a fragrance product in dependence of its matrix such as water-based or detergent-based products. Examples of the detergent-based products may include, but are not limited to, fabric conditioners, cleansing compositions, shampoos, and ethanol-based products, such as eau de toilette, eau de parfum, or emulsion-based products like creams.

The proposed computer-implemented method may be suitable for generating evaporation profiles of a fragrance product on a solid substrate, such as skin, clothes, paper, plastic, wood, or metal.

The proposed computer-implemented method may be used for exchanging ingredients in a fragrance product, which are blocked due to competitive intellectual property rights, regulatory issues in different countries or lack of resources.

The proposed computer-implemented method may reduce development costs by giving accurate predictions of temporal evaporation profiles so that time and cost consuming reassessments of fragrance compositions can be significantly reduced. A contribution thereby may be the reduction of waste material due to the reduced numbers of mixing steps for testing and olfactory evaluation.

A fragrance product may refer to a product comprising a fragrance composition and a matrix. The fragrance composition may comprise one or more fragrance ingredient(s). In other words, a fragrance product comprises a fragrance composition in a matrix comprising one or a plurality of fragrance ingredient(s). A fragrance product may comprise a fragrance composition in a matrix comprising a plurality of fragrance ingredients.

An interaction coefficient may refer to a correction factor linking ideal conditions with real behavior of substances in condensed phase. This deviation may be expressed by an activity coefficient. The activity coefficient may depend on the composition of the condensed phase.

A temporal evaporation profile of the fragrance product or the fragrance composition in the matrix may refer to a time-dependent quantity related to or associated with the evaporation behaviour of each fragrance ingredient. The time-dependent quantity may relate to an evaporation behaviour of each fragrance ingredient of the fragrance product or composition. The time-dependent quantity may relate to the behaviour of each fragrance ingredient of the fragrance product or composition in the gas and/or condensed phase. The time-dependent quantity may relate to a fractural amount of each fragrance ingredient in the gas phase and the condensed phase of the fragrance composition in the matrix. The fractural amount may be a fraction e.g. of 1 or 100% of the fragrance composition. The temporal evaporation profile may relate to an evaporation behaviour of each fragrance ingredient in the fragrance composition, wherein the effect of the matrix on the evaporation behaviour of the fragrance ingredients or interactions with the matrix is considered. The time dependent quantity may relate to partial vapour pressure, bloom, boost, substantivity or tenacity. The temporal evaporation profile may include one or more time-dependent quantities. The temporal evaporation profile may include one or more temperature-dependent quantities. The temporal evaporation profile may include one or more time-dependent quantities and one or more temperature dependent quantities.

The fragrance composition data may specify the fragrance composition. The fragrance composition data may specify one or more fragrance ingredients of the fragrance composition. The fragrance composition data may include a fragrance ingredient identifier for each fragrance ingredient comprised in the fragrance composition. The fragrance composition data may include an absolute or relative amount for each fragrance ingredient. The ingredient identifier may be associated with the respective absolute or relative amount. The fragrance ingredient identifier may be associated with a single chemical substance or a combination of chemical substances. The fragrance ingredient identifier may be associated with a fragrance ingredient having natural, semi-synthetic or synthetic origin. The fragrance ingredient identifier may be associated with a combination of fragrance ingredients. For such combination a sub-formula may specify a variable or fixed ratio of more than one fragrance ingredients. The sub-formula may be associated with one fragrance ingredient identifier. The fragrance composition specified by fragrance composition data may include the sum of all fragrance ingredients without solvent. The sum of relative amounts associated with the fragrance ingredient identifiers may add to 100 wt % of the fragrance composition. For a perfume composition for example, the fragrance composition data may specify a pure perfume oil.

The fragrance composition data may specify a representation of the molecular structure and/or a molecular geometry associated with each fragrance ingredient. The fragrance ingredient identifier may be associated with representation of the molecular structure and/or molecular geometry of the respective fragrance ingredient. This way the fragrance composition data may signify the composition of the fragrance composition and/or properties of fragrance ingredients.

The matrix data may specify the matrix. The matrix data may specify one or more matrix component(s). The matrix data may include a matrix identifier or a matrix component identifier for each matrix component. The matrix data may include an absolute or relative amount for each matrix component identifier. The matrix data may include an absolute or relative amount in relation to the fragrance composition. The matrix data may specify components of the fragrance product that do not add to the olfactive impression. Components of the fragrance product can either be attributed to the matrix data or to the fragrance composition data. In the latter case such components thereby may be subjected to the method of the present invention for identifying their good or bad non-odour effects in the temporal evaporation or odour profile, such as e.g. balming effects or caustic or toxic effects.

The matrix component identifier may be associated with liquid or solid matrix component. The matrix component identifier may be associated with a solvent, which may comprise water, alcohol, oil, detergent or mixtures thereof, or a substrate, which may be skin, textiles, paper, wood, plastics, such as polymers or plastic composite materials, metals or composite materials, or with mixture(s) of solvent(s) and substrate(s).

The fragrance composition data and the matrix may specify the fragrance ingredients, the matrix components, amounts and/or relative proportions.

The fragrance composition data may include vapour pressure for each fragrance ingredient. The vapor pressure may be associated with the ingredient identifier. The vapour pressure for each fragrance ingredient may be retrieved from a database based on the fragrance composition data. In a preferred embodiment the vapour pressure for each fragrance ingredient may be determined based on the molecular geometry representation.

The molecular geometry representation may be provided to determine vapor pressure for each fragrance ingredient. The molecular geometry representation for the fragrance ingredient may be obtained from a chemical file format as a functional of a local electron density associated with the fragrance ingredient. The molecular geometry representation for the fragrance ingredient may be determined based on a quantum mechanical model calculation. The molecular geometry representation for the fragrance ingredient may be determined, depending on the matrix using a quantum chemical model. Such quantum chemical model may include the solvent or matrix effect on the molecular geometry representation, such as intermolecular interactions. In addition, an ensemble of conformers in the solvent or matrix may be considered. Suitable quantum chemical models for the calculation of the molecular geometry are e.g. density functional theory (DFT), semi-empirical quantum chemical models, Hartree-Fock, or post-Hartree-Fock, preferably density functional theory (DFT).

The vapour pressure for each fragrance ingredient may be determined based on the molecular geometry representation using a quantum chemical model or a thermodynamic model.

The composition of the gas phase and the condensed phase, the interaction coefficients for each fragrance ingredient, the (partial) vapour pressure for each fragrance ingredient, the fugacity for each fragrance ingredient, the time-dependent quantity associated with the evaporation behaviour, or the fractural amount for each fragrance ingredient may be calculated in a time dependent manner. For instance for a first point in time:

the composition or amount of each fragrance ingredient in the gas phase and in the condensed phase is determined;

based on the determined composition or amount of each fragrance ingredient in the gas and condensed phase, the interaction coefficient, the time-dependent quantity or the relative amount of each fragrance ingredient is determined.

Hence after an initial determination of the composition of the gas phase and the condensed phase, the interaction coefficients for each fragrance ingredient, the partial vapour pressure for each fragrance ingredient, the fugacity for each fragrance ingredient, the time-dependent quantity for each fragrance ingredient or the fractural amount for each fragrance ingredient, the composition of the gas phase and the condensed phase, the interaction coefficients for each fragrance ingredient, the partial vapour pressure for each fragrance ingredient, the fugacity for each fragrance ingredient, the time-dependent quantity for each fragrance ingredient or the fractural amount for each fragrance ingredient may be updated by evolving the composition of the gas phase and the condensed phase in time. This way the changes in activity for each fragrance ingredient may be accounted for, as the mixture of the composition changes over time because of the distinct evaporation of the ingredients into the gas phase. Such a temporal altering condensed phase composition significantly influences intermolecular interactions. This important fact is accounted for by updating the interaction coefficients of every ingredient along the time axis.

In one embodiment the determination of the composition of the gas phase and/or condensed phase is adapted by including one or more of diffusion parameters to determine bloom and/or volume and/or radiance of the perceived odour impression, temperature dependence of the odorous experience, odour values, partition functions in case of multiphase matrices and/or explicit and ingredient specific dipolar, dispersive and H-bonding interactions with their environment. Bloom and/or volume or radiance is the perceived intensity of a fragrance composition or ingredient at some distance from the source (e.g. 1 m) and within a short period of time (e.g. up to 1 min). Volume or radiance is the property of a fragrance composition or ingredient to be perceived at some distance from the source (e.g. 1 m) for a prolonged time (e.g. up to 8 hours). The determination of the composition of the gas phase and/or condensed phase may further include i) diffusion parameters to determine the bloom and/or volume or radiance of the perceived odor impression, and/or ii) temperature parameters to determine temperature dependence of the odorous experience, and/or iii) odor values to determine the impact of certain fragrance ingredients, and/or iv) partition functions to determine the impact of multiphase matrices (e.g. dispersions), and/or v) explicit and component specific dipolar, dispersive and H-bonding interactions with their environment to determine the tenacity and in combination with odor thresholds the substantivity.

The temporal evaporation profile may be related to a time-dependent fractural amount of each fragrance ingredient in the gas phase and/or the condensed phase of the fragrance composition in the matrix over the predetermined period of time.

The generated temporal evaporation profile may be usable for monitoring quality of the fragrance product in a production process and/or for validating the production of the fragrance product based on at least one precursor, such a new matrix component or fragrance ingredient, substrate. The temporal evaporation profile may be used for monitoring quality of the fragrance product in a production process and/or for validating the production quality of the fragrance product based on at least one precursor and/or substrate. Validating the fragrance composition or product may be based on the temporal evaporation profile associated with at least one new precursor and/or at least one substrate. The generated temporal evaporation profile may be provided for validating and/or monitoring the fragrance product or composition with respect to the performance characteristic. The generated temporal evaporation profile may be provided to validate and/or monitor the fragrance product or composition with respect to the performance characteristic. The generated temporal evaporation profile, which when provided to a validation apparatus, may validate and/or monitor the fragrance product or composition with respect to the performance characteristic.

The performance characteristic may relate to a physical, chemical or physio-chemical characteristic. The performance characteristic may relate to an olfactory characteristic. The performance characteristic may comprise one or more physical, chemical or physio-chemical characteristic (s) directly or indirectly related to olfactory characteristic(s) of the fragrance product.

According to an embodiment of the present invention, the fragrance ingredients are grouped into a plurality of odour families in accordance with their olfactive contributions. The temporal evaporation profile further comprises a time-dependent fractural amount of each odour family in the gas phase and the condensed phase of the fragrance composition in the matrix over the predetermined period of time.

For example, each fragrance ingredient may have a description that indicates the respective odour family. The description is a nominal measurement scale (categories). For the characterization of odour, a reference vocabulary for taste and odour sensation may be used. One example of the odour description is the Odour Descriptor Wheel. For perfume fragrance compositions, the odour description of the fragrance ingredients may be categorised as main descriptions and sub-descriptions. Examples of the main descriptions may include, but are not limited to, fruity, green, marine, floral, woody, ambery, and spicy. Examples of the sub-descriptions of the main description "fruity" may include, but are not limited to, apple, lemon, citrus, strawberry, cherry, and grapes.

In some examples, descriptions of the odour families and their contribution to the total olfactive perceptions may be already known and can be retrieved from databases. Such databases may be commercially available databases such as e.g. ScenTree, Flavornet, GoodScents, SuperScent, Sigma-Aldrich, or an internal database.

In some examples, the descriptions of the odour families of a specific fragrance ingredient may be not available from a database. In such cases, the descriptions of the odour families of said fragrance ingredient may be predicted using machine-learning algorithms. These algorithms are preferably trained on a computer-readable 2D description of the molecular structure to identify lead structures in the molecular structure of the fragrance ingredients, which contribute to the olfactive perception of the fragrance ingredients.

According to an embodiment of the present invention, each fragrance ingredient has a description indicative of the respective odour family. The description of each fragrance ingredient is obtained from a database or predicted using a machine-learning algorithm.

According to an embodiment of the present invention, the method further comprises the step of validating, based on the determined temporal evaporation profile, the fragrance product comprising a fragrance composition and a matrix with respect to a performance characteristic.

The performance characteristic may comprise a desired temporal evaporation profile of a fragrance composition.

According to an embodiment of the present invention, in step b) the molecular geometry of each fragrance ingredient is determined using a quantum chemical model.

For example, the molecular geometry of each fragrance ingredient may be calculated using density functional theory (DFT), semi-empirical quantum chemical models, Hartree-Fock, or post-Hartree-Fock, preferably density functional theory (DFT).

According to an embodiment of the present invention, in step b) the molecular geometry of each fragrance ingredient is optimized using a generalized gradient approximation density functional theory method, whereby the matrix effect is included by utilizing a quantum chemical model.

Equilibrium structures may be preferably optimized using a generalized gradient approximation (GGA) density functional theory (DFT) method employing e.g. Ahlrich's basis set. The solvent or matrix effect on the molecular geometry, usually via intermolecular interactions, such as hydrogen bonding, ionic bonding, dipole forces or van der Waals forces, may be preferably represented utilizing a polarizable continuum model, microsolvation, or a cluster continuum model.

According to an embodiment of the present invention, in step c) the vapour pressure of each fragrance ingredient is determined using a quantum chemical model or a thermodynamic model.

For calculating the vapour pressures of each neat fragrance ingredient using a quantum chemical model, it may use the chemical potentials in condensed and in gas phase obtained by a conductor-like screening model for real solvents (COSMO-RS) or COSMO-SAC. The COSMO method is a calculation method for determining the electrostatic interaction of a molecule with a solvent. Further information of the COSMO method can be found in A., Klamt; G., Schüürmann (1993). "COSMO: a new approach to dielectric screening in solvents with explicit expressions for the screening energy and its gradient". J. Chem. Soc. Perkin Trans.2. 2 (5): 799-805. Further information of the COSMO-RS method can be found in "COSMO-RS: From quantum Chemistry to Fluid Phase Thermodynamics and Drug Design", A. Klamt, Elsevier: Amsterdam, 2005.

In an alternative approach the vapour pressures of each neat fragrance ingredient may be calculated using a thermodynamic model. A suitable thermodynamic model is based on an equation of state. Any equation of state suitable for calculating the vapour pressure of the neat fragrance ingredients may be used.

According to an embodiment of the present invention, in step c) the vapour pressure of each fragrant ingredient is determined at a certain temperature, pressure, and/or relative humidity.

In other words, the vapour pressures of each neat fragrance ingredient may be calculated under certain conditions of temperature, pressure and/or relative humidity, usually applying ambient conditions of 15-25° C. temperature, atmospheric pressure and 40-60% relative humidity. However, also different conditions at higher or lower temperature, pressure or relative humidity may be applied.

For example, the vapour pressure of each fragrant ingredient may be determined at a certain temperature, pressure and relative humidity using the chemical potentials of each fragrant ingredient in the condensed phase and the gas phase obtained by COSMO-RS or COSMO-SAC.

According to an embodiment of the present invention, in step d), the time-dependent activity coefficient of each fragrance ingredient is determined utilizing a quantum-chemical model or a thermodynamic model.

In some examples, the time-dependent activity coefficients of each fragrance ingredient in a given mixture over the predetermined period of time may be determined utilizing a quantum-chemical model, such as COSMO-RS that is based on chemical potentials in condensed phase of the fragrance composition in a matrix, which in turn rely on quantum chemical input.

Alternatively, these time-dependent activity coefficients may be calculated based on a thermodynamic model, such as uniquac functional-group activity coefficients (UNIQUAC), thereby utilizing group-contribution methods, such as UNIFAQ (universal quasichemical). Further information of UNIQUAC may be found in Aage Fredenslund, Russell L. Jones and John M. Prausnitz, "Group-Contribution Estimation of Activity Coefficients in Nonideal Liquid Mixtures", AlChE Journal, vol. 21 (1975), p. 1086. Further information of UNIFAQ may be found in Aage Fredenslund, Jürgen Gmehling and Peter Rasmussen, Vapor-liquid equilibria using UNIFAC: a group contribution method, Elsevier Scientific, New York, 1979.

According to an embodiment of the present invention, in step e) the determination of the time-dependent fractural amount of each fragrance ingredient in a gas phase of the fragrance composition in the matrix is adapted by including one or more of: a diffusion parameter, temperature dependence of an odorous experience, an odor value, a partition function in case of multiphase matrices, and explicit and component specific dipolar, dispersive and H-bonding interactions with their environment.

In other words, the proposed computer-implemented method for determining the composition of the gas phase and/or condensed phase allows for easily extending its accuracy by including i) diffusion parameters to model the bloom and/or volume or radiance of the perceived odor impression, and/or ii) including temperature dependence of the odorous experience, and/or iii) including odor values to more accurately model the impact of certain fragrance components, and/or iv) including partition functions in case of multiphase matrices (e.g. dispersions), and/or v) including explicit and component specific dipolar, dispersive and H-bonding interactions with their environment to better model their tenacity and in combination with odor thresholds their substantivity.

According to an embodiment of the present invention, the composition of the condensed phase is determined by repeating the steps of:
  removing an aliquot of the gas phase being at thermodynamic equilibrium with the condensed phase;
  altering the composition of the condensed phase during the subsequent thermodynamic equilibration between the gas phase and the condensed phase;
  repeating the previous steps until the composition of the condensed phase is significantly altered at a time point over the predetermined period of time;
  recalculating the time-dependent activity coefficient of the altered condensed phase at the time point over the predetermined period of time.

According to an embodiment of the present invention, the matrix is selected from a solvent, a substrate, or a mixture of a solvent and a substrate.

Examples of the solvent may include, but are not limited to, water, alcohol, oil, detergent, and mixtures thereof.

Examples of the substrate may include, but are not limited to, skin, textiles, paper, wood, plastics, metals, and composite materials.

According to an embodiment of the present invention, the fragrance ingredients of the fragrance composition are received for determining the molecular geometry in form of a chemical file format.

Chemical file formats are computational data formats for coding chemical information. The Simplified Molecular Input Line Entry Specification (SMILES) is a line notation for molecules. SMILES strings include connectivity but do not include 2D or 3D coordinates.

The XYZ format is a simple format that usually gives the number of atoms in the first line, a comment on the second, followed by a number of lines with atomic symbols (or atomic numbers) and cartesian coordinates.

The MDL number contains a unique identification number for each reaction and variation. The format is RXXXnnnnnnnn. R indicates a reaction, XXX indicates which database contains the reaction record. The numeric portion, nnnnnnnn, is an 8-digit number.

SDF and MOL are other file formats from MDL Information Systems. The molfile consists of some header information, the Connection Table (CT) containing atom info, then bond connections and types, followed by sections for more complex information. "SDF" stands for structure-data file, and SDF files actually wrap the molfile format. Multiple compounds are delimited by lines consisting of four dollar signs ($$$$). A feature of the SDF format is its ability to include associated data such as e.g. molecular weight.

According to a second aspect of the present invention, there is provided a device comprising a processing unit configured to perform the steps of the method according to the first aspect and any associated example.

According to a third aspect of the present invention, there is provided a computer program element comprising instructions which, when executed by a processing unit, cause the processing unit to carry out the steps of the method according to the first aspect and any associated example.

The term "fragrance composition" as used herein may refer to any kind of composition comprising a plurality of volatile ingredients, which contribute to an olfactive impression, caused by interaction with the olfactory receptor cells in the olfactory epithelium of the nasal cavity of humans or animals. The olfactive impression can be a pleasant impression, qualifying the odour as pleasant odour, or an unpleasant odour, qualifying the odour as malodour. A misodour or off-odour is an odour, which was not intended. If a fragrant ingredient is odourless (i.e. not contributing to the olfactive impression) it is attributed to the matrix.

The term "matrix" as used herein may refer to a substance, which is in contact with the fragrance composition but itself does may not contribute or may be irrelevant for the purpose of the product to the olfactive impression of the fragrance composition. The matrix can be liquid or solid and can be selected from solvents, which comprise water, alcohol such as ethanol, oil, detergent or mixtures thereof, or substrates, which are selected from skin, textiles, paper, wood, plastics (such as polymers, plastic composites etc.), metals or composite materials, or mixtures of solvents and substrates. Although not directly contributing to the olfactive impression of the fragrance composition the matrix can interact with the fragrance composition via intermolecular interactions of the components of the matrix with the ingredients of the fragrance composition, thus accelerating or slowing down the evaporation of different ingredients of the fragrance composition (boosting and retarding behaviour), and thereby can alter the olfactive impression of the fragrance composition. If an ingredient, originally attributed to the matrix, turns out to contribute to the olfactive impression, it is classified as an olfactive fragrance ingredient and attributed to the fragrance composition.

The "molecular geometry" of a chemical molecule, especially a fragrance ingredient, as used herein may refer to the three-dimensional shape of the molecule based on its orientation due to the intramolecular interactions of the covalent bonds and the intermolecular interactions, such as hydrogen bonding, ionic bonding, dipole forces or van der Waals forces, with other molecules, especially molecules of the matrix. The molecular geometry is constituted as a function of spatially dependent electron density and can be calculated using quantum chemical models/methods such as density functional theory (DFT), Hartree-Fock (HF), post-Hartree-Fock or semi-empirical quantum chemical models.

The term "vapour pressure", also referred to as equilibrium vapour pressure, as used herein, may refer to the pressure exerted by a vapour in thermodynamic equilibrium with its condensed phases (solid or liquid) at a given temperature in a closed system. The equilibrium vapour pressure is an indication of a liquid's evaporation rate. It relates to the tendency of particles to escape from the liquid (or a solid)."

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the invention.

DETAILED DESCRIPTION OF THE INVENTION

Figure 1:
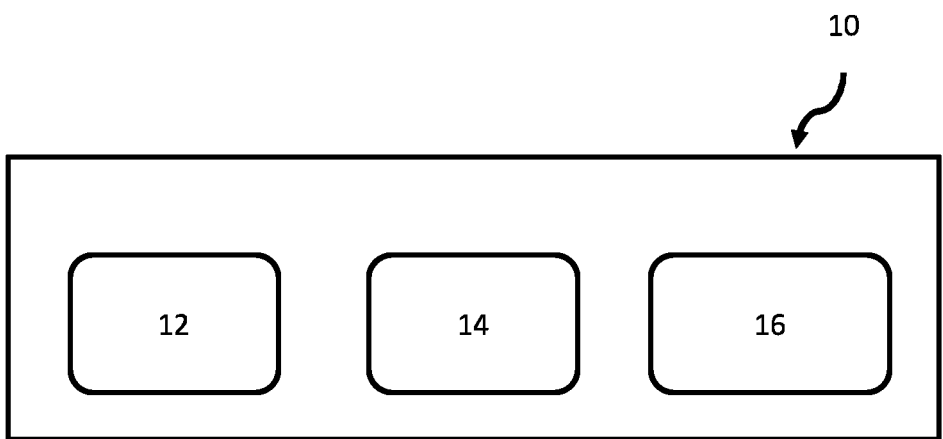
FIG. 1 illustrates a block diagram of an exemplary device for generating or predicting a temporal evaporation profile of a fragrance product comprising a fragrance composition and a matrix comprising a plurality of fragrance ingredients.

FIG. 1 illustrates a block diagram of an exemplary device 10 for generating or predicting a temporal evaporation profile of a fragrance product comprising a plurality of fragrance ingredients.

The device 10 may include one or more processing units 12. Optionally, as shown in FIG. 1, the device 10 may include a memory 14, and one or more communications modules 16.

In general, the device 10 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 1 may show a limited number of components by way of example, it can be appreciated that a greater or a fewer number of components may be employed for a given implementation.

In some examples, the device 10 may be implemented by a computing platform such as a mobile platform, personal computer (PC) platform, and/or consumer electronics (CE) platform supporting various networking, communications, and/or multimedia capabilities. Such capabilities may be supported by various networks, such as a Wide Area Network (WAN), Local Area Network (LAN), Metropolitan Area Network (MAN), wireless WAN (WWAN), wireless LAN (WLAN), wireless MAN (WMAN), wireless personal area network (WPAN), Worldwide Interoperability for Microwave Access (WiMAX) network, broadband wireless access (BWA) network, the Internet, and/or any other wired or wireless network in accordance with the described embodiments.

In some implementations, the device 10 may comprise a system within and/or coupled to a computing device such as PC, desktop PC, notebook PC, laptop computer, mobile internet device (MID), mobile computing device, smart phone, personal digital assistant (PDA), mobile telephone, or other type of computing device in accordance with the described embodiments. The computing device may include, for example, an electronic display.

The processing unit(s) 12 may execute instructions to perform the method described herein, which will be explained in detail with respect to the embodiment shown in FIG. 2.

The memory 14 may include, but is not limited to, volatile memory and/or non-volatile memory. The memory 14 may be used to store processor instructions, and other data and instructions to enable the processor to perform the techniques described herein.

The one or more communications modules 16 may include hardware and/or software to enable the device 10 to receive a user input that defines the fragrance ingredients of the fragrance composition and the matrix, and to communicate with other devices and/or a network. For example, the one or more communications modules 16 may receive the user input via a wired connection or via a wireless connection. The one or more communications modules 16 may also provide cellular telephone communications, and/or other data communications for the device 10.

Figure 2:
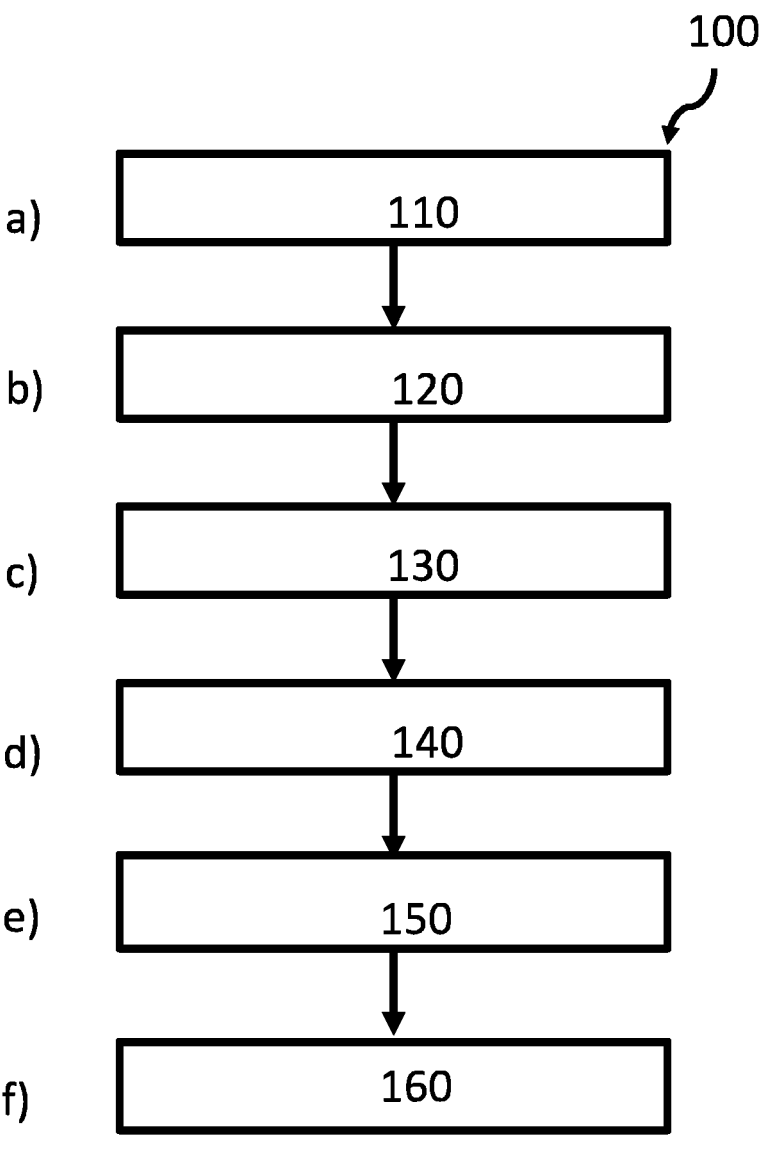
FIG. 2 illustrates a flow chart describing a computer-implemented method for generating or predicting a temporal evaporation profile of a fragrance product comprising a fragrance composition and a matrix comprising a plurality of fragrance ingredients

FIG. 2 illustrates a flow chart describing a computer-implemented method 100 for predicting or generating a temporal evaporation profile of a fragrance product comprising a fragrance composition, comprising a plurality of fragrance ingredients, and a matrix, in accordance with an embodiment. Beginning at block 110 i.e. step a), an apparatus, such as device 10 shown in FIG. 1, receives a measurement or user input that defines the fragrance ingredients of the fragrance composition and the matrix. All fragrance ingredients of the fragrance composition may be defined by listing them and defining their amounts in the fragrance composition. A fragrance ingredient thereby can be a single chemical substance or a combination of chemical substances. The fragrance ingredients can have natural, semi-synthetic or synthetic origin. It is also possible to use a sub-formula, i.e. a combination of fragrance ingredients that are used in a fix ratio, and to add such a sub-formula as one ingredient. The fragrance composition is thereby defined as the sum of all fragrance ingredients without solvent, thus the sum of all fragrance ingredients making up 100 wt % of the fragrance composition. For a perfume composition for example, the fragrance composition is reflected by the pure perfume oil.

Components of the matrix adding to the olfactive impression are attributed to the fragrance composition. Fragrance ingredients not adding to the olfactive impression can either be attributed to the matrix or to the fragrance composition and thereby subjected to the method of the present disclosure for identifying their good or bad non-odour effects in the temporal evaporation profile, such as e.g. balming effects or caustic or toxic effects.

Further, the matrix is defined. The matrix may be liquid or solid. In some examples, it is selected from solvents, which comprise water, alcohol, oil, detergent or mixtures thereof, or substrates. In some examples, it is selected from substrates, such as skin, textiles, paper, wood, plastics, such as polymers or plastic composite materials, metals or composite materials. In some examples, it is selected from mixtures of solvents and substrates.

Depending on the application of the fragrance composition, such as e.g. a perfume oil, the matrix may be a solvent, such as ethanol, water, oil or detergent or mixtures thereof used for the preparation of e.g. an eau de parfum, eau de toilette, a hair shampoo, a shower or washing lotion, a soap or a body cream. When defining a solvent or mixture of solvents as matrix the amount of the solvent(s) usually are also defined.

The method of the present disclosure may be used for generating or predicting the temporal evaporation profile of a fragrance product on a solid substrate, such as e.g. skin, textiles, paper wood, plastics metals or composite materials, only to mention view examples.

The fragrance ingredients, their amounts and the matrix may be defined by preparing a list of the names of the selected ingredients and matrix components usually together with their relative proportions such as e.g. in a spread sheet. The list can be put into the apparatus, e.g. device 10, via an input unit. The list can also be downloaded from a database.

At block 120 i.e. step b), the molecular geometry of each fragrance ingredient is provided or determined depending on the matrix by the apparatus (e.g. device 10 shown in FIG. 1). This could be done using a quantum chemical model. Suitable quantum chemical models for the calculation of the molecular geometry are e.g. density functional theory (DFT), semi-empirical quantum chemical models, Hartree-Fock, or post-Hartree-Fock, preferably density functional theory (DFT).

The fragrance ingredients of the fragrance composition are preferably received for calculating the molecular geometry in form of chemical file formats such as SMILES code, XYZ, MDL mol or SDF.

Thereby, when using quantum chemical models such as density functional theory, the molecular geometry of the fragrance ingredient is obtained from the chemical file format as a functional of the local electron density.

It is preferred that the molecular geometry is obtained from the calculation as equilibrium structure.

All equilibrium structures are preferably optimized using a generalized gradient approximation (GGA) density functional theory (DFT) method employing e.g. Ahlrich's basis set. The solvent or matrix effect on the molecular geometry, usually via intermolecular interactions, such as hydrogen bonding, ionic bonding, dipole forces or van der Waals forces, is preferably represented utilizing a polarizable continuum model, microsolvation, or a cluster continuum model.

Parallel to optimizing the geometries of a fragrance ingredient, a conformational search can be employed to find the best conformer or an ensemble of conformers that can be weighted by Boltzmann distribution. The solvent or matrix effect may efficiently be calculated and represented by the conductor-like screening model.

Calculating an ensemble of the most relevant conformers in a particular solvent or matrix may ensure capturing the most important fragrance-matrix interactions that significantly influence physico-chemical properties, such as the vapor pressure or deviations to ideal behavior in condensed matter.

At block 130, i.e. step c), after calculating the molecular geometries of each fragrance ingredient as discussed above the calculated molecular geometries, preferably the optimized geometries of an ensemble of conformers, are used for calculating the vapour pressures of each neat (or pure) fragrance ingredient using a quantum chemical model or a thermodynamic model.

Thereby, the vapour pressures of each neat fragrance ingredient are preferably calculated under certain conditions of temperature, pressure and relative humidity, usually applying ambient conditions of 15-25° C. temperature, atmospheric pressure and 40-60% relative humidity. However, also different conditions at higher or lower temperature, pressure or relative humidity can be applied.

For calculating the vapour pressures of each neat fragrance ingredient using a quantum chemical model it is preferred to use the chemical potentials in condensed and in gas phase obtained by a conductor-like screening model for real solvents (COSMO-RS) or COSMO-SAC. Systematic errors of absolute vapour pressures may be corrected by adding experimental boiling points to the quantum chemical-based thermodynamic model. The vapour pressure of a neat fragrance ingredient may be calculated based on its single (preferably best or lowest-energy) conformer or based on an ensemble of Boltzmann-weighted conformers.

By including an ensemble of conformers and—if available—the experimental boiling points of the fragrance ingredient the accuracy of the pure fragrance ingredient's vapour pressure is augmented.

In an alternative approach the vapour pressures of each neat fragrance ingredient are calculated using a thermodynamic model. A suitable thermodynamic model is based on an equation of state. Any equation of state suitable for calculating the vapour pressure of the neat fragrance ingredients can be used.

When using a thermodynamic model, usually process step b) can be omitted as superfluous as the suitable thermodynamic models usually are based on empirical data.

Preferably, the vapour pressures of each neat fragrance ingredient may be determined using a quantum chemical model, preferably as described above. The reason is that for quantum chemical models in contrast to the thermodynamic models based on equations of state no experimental data is needed. This gives the flexibility of adjustments to different matrices or fragrance ingredients without further measurement requirements and hence makes the validation of fragrance compositions with new fragrance ingredients or new matrices possible. Complex measurements are hence not needed, if e.g. the production line is changed. In addition in case of frequent product changes the validation procedure is easily adaptable. This new invention enables fast and easy scent design using digital communication channels for sharing the generated or predicted performance results, assuring consistent data formats or architectures that in turn provide maximal comparability and consistency and allow for effective data governance.

At block 140, i.e. step c), in addition to the calculation of the vapour pressures for each neat fragrance ingredient, the time-dependent activity coefficients of each fragrance ingredient for the mixture of the condensed phase is determined on the fly over a predetermined period of time while the mixture in the condensed phase changes.

The time-dependent activity coefficient may link ideal with real behavior of substances in condensed phase. This deviation is expressed by the time-dependent activity coefficient. It is favorable when dealing with mixtures in which the composition changes over time e.g. due to different evaporation behavior of components (e.g. odorous oils). The time-dependent activity coefficients of each fragrance ingredient in a given mixture at $t_0$ and $t_1$-$t_x$ are preferably calculated utilizing a quantum-chemical model, such as the conductor-like screening model for real solvents (COSMO-RS) that is based on chemical potentials in condensed phase of the fragrance composition in a matrix, which in turn rely on quantum chemical input.

Alternatively, these activity coefficients may be calculated based on a thermodynamic model, such as UNIQUAC, thereby utilizing group-contribution methods, such as UNIFAQ.

The time-dependent activity coefficients of every ingredient in the mixture may be calculated in the beginning ($t_0$) and are updated in certain intervals over time ($t_1$-$t_x$) as the composition of the mixture of the condensed phase alters due to distinct evaporation of fragrant ingredients into the gas phase from the condensed phase mixture.

More important than the concentration of a fragrant ingredient in the condensed phase is the activity that changes, as the mixture of the composition changes over time because of the distinct evaporation of the ingredients into the gas phase. Such a temporal altering condensed phase composition significantly influences intermolecular interactions. This important fact is accounted for by updating the time-dependent activity coefficients of every ingredient along the time axis. This is preferably done on-the-fly in the backend of the program.

At block 150, i.e. step e), from the calculated vapour pressures and activity coefficients of each fragrant ingredient, a time-dependent fractural amount of each fragrance ingredient in the gas phase and the liquid phase of a fragrance composition is determined over the predetermined period of time, e.g. at the initial time to and the predetermined times $t_1$-$t_x$, to generate a temporal evaporation profile of the fragrance composition in the matrix.

The gas phase composition may be preferably derived from thermodynamic equilibrium calculations assuming ideal gas-phase behaviour preferably based on the relationship expressed by extended Raoult's law $$y_i \Phi_{p,i} p = x_i \gamma_i p_i^*$$

with $x_i$ being the mole fraction of component i in the liquid phase, $y_i$ being the mole fraction of component i in the gas phase, $p_i^*$ being the vapour pressure of the neat component i, p being the total pressure, $\Phi_{p,i}$ being the fugacity coefficient of component i and $\gamma_i$ being the time-dependent activity coefficient of the component i. The fugacity coefficient $\Phi_{p,i}$ is set to unity, assuming ideal gas-phase behavior in a first approximation, most importantly due to low pressures applied (ambient pressure).

It may be preferred that the composition of the condensed phase is determined by repeating the steps of removing an aliquot of the gas phase being at thermodynamic equilibrium with the condensed phase;

altering the composition of the condensed phase during the subsequent thermodynamic equilibration between the gas phase and the condensed phase;

repeating the previous steps until the composition of the condensed phase is significantly altered at time $t_1$-$t_x$;

recalculating the time-dependent activity coefficient of the altered condensed phase at the time $t_1$-$t_x$.

The aliquot of the gas phase to be removed thereby can be a proportion of the gas phase or the total gas phase. In a first approximation the total gas phase can be removed. It has been found that removing the total gas phase is sufficiently accurate and simplifies the calculation.

Usually, when calculating the time-dependent activity coefficients and composition of the gas phase ambient conditions of 15-25° C. temperature, atmospheric pressure and 40-60% relative humidity are applied. However, also different conditions at higher or lower temperature, pressure or relative humidity can be applied.

Optionally, for the method of the present disclosure the same conditions of temperature, pressure and relative humidity may be applied for all calculations.

Preferably, the determination of the composition of the gas phase and/or condensed phase is adapted by including one or more of diffusion parameters to model bloom and/or volume or radiance of the perceived odour impression, temperature dependence of the odorous experience, odour values, partition functions in case of multiphase matrices and/or explicit and ingredient specific dipolar, dispersive and H-bonding interactions with their environment.

Thereby, bloom and/or volume or radiance is the perceived intensity of a fragrance composition at some distance from the source (e.g. 1 m) and within a short period of time (e.g. up to 1 min).

This proposed method for determining the composition of the gas phase and/or condensed phase may allow for easily extending its accuracy by including i) diffusion parameters to model the bloom and/or volume or radiance of the perceived odor impression, and/or ii) including temperature dependence of the odorous experience, and/or iii) including odor values to more accurately model the impact of certain fragrance components, and/or iv) including partition functions in case of multiphase matrices (e.g. dispersions), and/or v) including explicit and component specific dipolar, dispersive and H-bonding interactions with their environment to better model their tenacity and in combination with odor thresholds their substantivity.

Optionally, the fragrance ingredients are grouped into odour families and their contribution to the total olfactive perception.

From several fragrance ingredients descriptions of the odour families and their contribution to the total olfactive perceptions is already known and can be retrieved from databases. Such databases can be commercially available databases such as e.g. ScenTree, Flavornet, GoodScents, SuperScent or Sigma-Aldrich or an internal database. Such a database usually lists the name and the structure of the fragrance ingredient together with several descriptions of the main and sub-odour families and optional additional attributes of the fragrance ingredient, such as e.g. molecular weight or boiling points, if available. Usually the number of descriptions of the fragrance ingredient varies from about 4 to 10.

In the case that the descriptions of the odour families of a specific fragrance ingredient is not available from a database the descriptions of the odour families of said fragrance ingredient can be predicted using machine-learning algorithms. These algorithms are preferably trained on a computer-readable 2D description of the molecular structure to identify lead structures in the molecular structure of the fragrance ingredients, which contribute to the olfactive perception of the fragrance ingredients. The prediction of the descriptions of the odour families of a fragrance ingredient using machine-learning algorithms is preferably conducted in a computer-implemented method using a processing unit comprising one or more processors as described above for the quantum chemical calculations.

Preferably, the descriptions of each fragrance ingredient for their contribution to the total olfactive perception are obtained from a database or predicted using machine-learning algorithms, the descriptions that are common for different fragrance ingredients are bundled in odour main families and optionally odour subfamilies, and their contribution to the total olfactive perception is summed up according to their fractional occurrence in the gas phase.

The fragrance ingredients may be grouped into odour families, whereby each fragrance ingredient is usually matched with 3 to 4 descriptions, which are either obtained from a database or predicted using machine-learning algorithms. For example the fragrance ingredient "ligustral" can be attributed with the descriptions green, herbaceous and citrus.

Then usually about 10 to 15 odour families are defined which in the end shall be listed in the resultant temporal odour families profile.

All amounts of the different descriptions of said defined 10 to 15 odour families may be added together. For example from 25 fragrance ingredients of the composition 5 fragrance ingredients are attributed with the description fruity and 3 fragrance ingredients are attributed with the description floral. Thereby, in a first approach each of the 3 to 4 descriptions which are selected for each fragrance ingredient is usually counted with the same weighting of olfactive perception of about 1. For example for the fragrance ingredient "ligustral" the olfactive perception of green is counted to be about the same as of herbaceous or citrus. The descriptions can also be weighted with different factors of olfactive perception such as e.g. for the fragrance ingredient "ligustral" the olfactive perception of green is counted to be 1, the olfactive perception of herbaceous is counted to be 0.4 and the olfactive perception of citrus is counted to be 0.2.

The contribution of the odour families to the total olfactive perception is summed up according to their fractional occurrence in the gas phase per time interval.

The sum of all odour families per time interval is listed in a table and preferably normalized to 1 or 100%. An excerpt of such a table at time intervals $t_1$, $t_2$ and $t_3$ for 8 descriptions before normalization can be seen below. It can be seen from the numbers that the odours described with the descriptions lavender, herbal and fresh contribute the most to the olfactive perception throughout the timeframe of $t_1$ to $t_3$. The contribution of the odour described with the description fruity increases from $t_1$ to $t_3$, whereas the contribution of other odours such as those described with the descriptions floral, *galbanum* or green are small but distinct.

| description | Time $t_1$ | Time $t_2$ | Time $t_3$ |
|---|---|---|---|
| fruity | 55443.8093 | 65242.8238 | 97911.6422 |
| floral | 1232.1055 | 1482.57624 | 2467.70061 |
| lavender | 176436.326 | 199267.005 | 248857.837 |
| bergamote | 7299.01625 | 8775.44308 | 14407.1832 |
| herbal | 140441.953 | 155891.897 | 178136.146 |
| galbanum | 220.798389 | 266.180989 | 442.890649 |
| green | 254.140349 | 306.424072 | 509.842608 |
| fresh | 140413.171 | 155857.313 | 178078.492 |

At block 160, i.e. step f), the determined temporal evaporation profile may be provided e.g. to a graphical user interface, to a printing unit for printing the temporal evaporation profile, and/or to a storing unit for storing the temporal evaporation profile.

For example, the temporal fragrance ingredient profile and/or the temporal odour families profile is displayed, based on the compositions of the gas phase at the predetermined times to, $t_1$-$t_x$ and grouping of the fragrance ingredients of the compositions of the gas phase, in order to visualize the temporal performance and olfactive perception of the fragrance composition in the matrix.

The temporal evaporation profiles can be displayed according to the special requirements of the user.

In some examples, the temporal evaporation profile over time can be displayed in a graph of the fractural amounts, such as the partial pressures, of all fragrance ingredients in the gas phase of the fragrance composition over time as calculated in process step f). Thereby, the total amount of all fragrance ingredients in the gas over time is usually normalized to either 1 or 100% and the fractural amounts are listed as fractions of 1 or 100%. These temporal fractural amounts can be displayed in a graph over time in colour codes. Said option of displaying the temporal evaporation profile is especially suitable for displaying the volatility of each fragrance ingredient of a fragrance composition in a specific matrix and their contribution to the temporal evaporation profile of said fragrance composition. It can be used e.g. when comparing a fragrance composition in different matrices and how the different matrices influence the volatility of different fragrance ingredients.

In some examples, the temporal evaporation profile can be displayed in a graph of the fractural amounts of all odour families in the gas phase of the fragrance composition over time. Thereby, the total amount of all odour families in the gas phase of the fragrance composition over time is usually normalized to either 1 or 100% and the fractural amounts are listed as fractions of 1 or 100% as discussed above. These temporal fractural amounts can be displayed in a graph over time in colour codes. Said option of displaying the temporal evaporation profile is especially suitable for displaying the development of the olfactive perception of a fragrance composition in a specific matrix and determine the odour development over time such as the top note, core note and bottom note of the fragrance composition in a specific matrix. Said odour development can then be compared to the odour development over time of the same fragrant composition in a different matrix. Additionally, any possible misodours or malodours, which may develop over time can be determined.

Optionally, the computer-implemented method may further comprise the step of validating, based on the determined temporal evaporation profile, the fragrance product with respect to a performance characteristic.

It will be appreciated that the above operation may be performed in any suitable order, e.g., consecutively, simultaneously, or a combination thereof, subject to, where applicable, a particular order being necessitated, e.g., by input/output relations.

Figure 3:
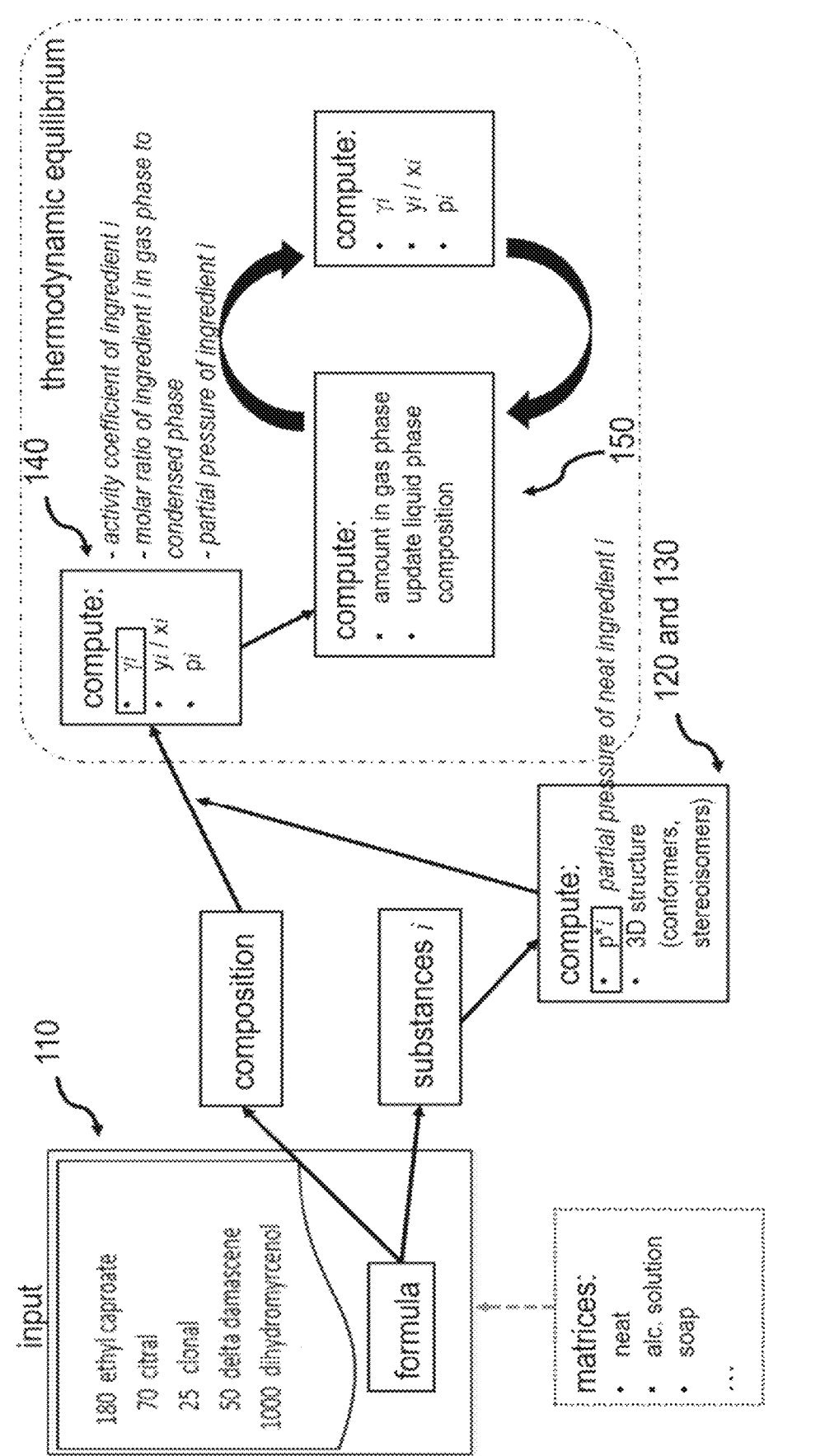
FIG. 3 shows an exemplary computer-implemented method.

FIG. 3 illustrates an exemplary computer-implemented method 100 for generating or predicting a temporal evaporation profile of a fragrance composition in a matrix comprising a plurality of fragrance ingredients.

Via the input unit, the composition is defined by introducing the ingredients together with their amounts at a block corresponding to block 110 in FIG. 2. Thereby, the ingredients are introduced in chemical file format such as in form of chemical file formats such as SMILES code, XYZ, MDL mol or SDF. Additionally, the matrix is defined, e.g. by defining the solvent, such as ethanol, together with its amount. The chemical file formats of the ingredients are used in the processing unit for calculating the molecular geometry of each ingredient depending on the matrix using quantum chemical calculations, preferably together with its conformers and stereoisomers, thereby selecting either the best conformer or an ensemble of conformers.

The molecular geometry, preferably the best conformer or an ensemble of conformers is then used for calculating the vapour pressures of each neat fragrance ingredient using quantum chemical calculations at a block corresponding to blocks 120 and 130 in FIG. 2.

The calculated data of each fragrance ingredient and the data of the fragrance composition such as the amounts of the different ingredients are then used for calculating the partial pressure $p_i$, the time-dependent activity coefficient $\gamma_i$ and the molar ratios $x_i$ and $y_i$ of each ingredient in the condensed phase and gas phase at the thermodynamic equilibrium at the beginning $t_0$. This corresponds to block 140 in FIG. 2.

From this data the fractural amounts of each ingredient in the gas phase at given time intervals $t_1$-$t_x$ are calculated by recalculating the partial pressure $p_i$, the time-dependent activity coefficient $\gamma_i$ and the molar ratios $x_i$ and $y_i$ of each ingredient in the condensed phase and gas phase at the thermodynamic equilibrium at said time intervals $t_1$-$t_x$ based on the different composition of the condensed phase over time. This corresponds to block 150 in FIG. 2.

Figure 4:
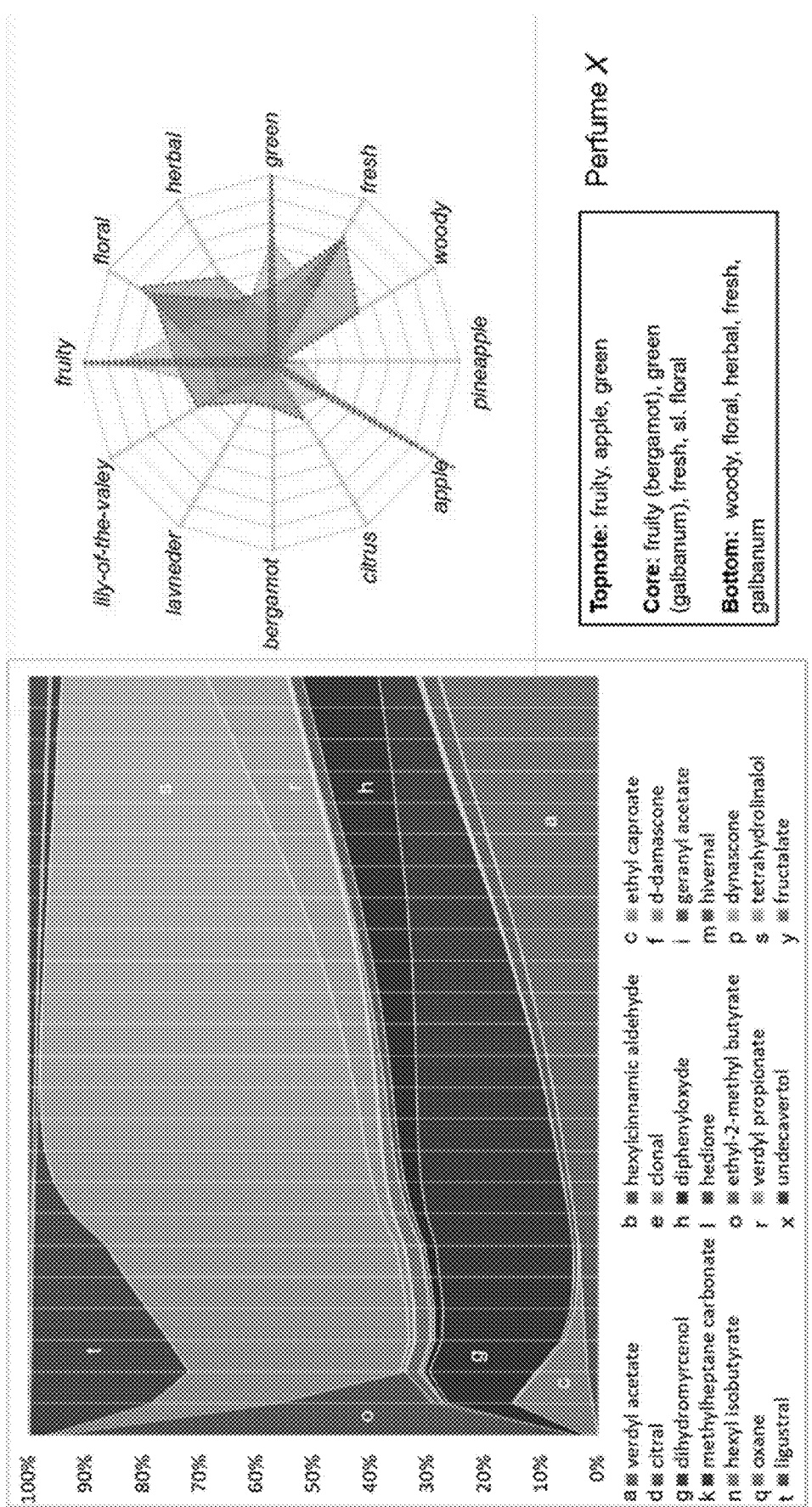
FIG. 4 shows the temporal evaporation profile of a perfume composition X predicted or generated with the method of the invention with the fragrance ingredients shown in the list on the left side together with their main odour descriptions. The temporal olfactive profile is summarized into an odour description of the top note, core and bottom note.

FIG. 4 shows the temporal evaporation profile of a perfume x in form of a temporal odour families' profile. The development of the fractural amounts of the different odour families in the gas phase over time are shown in colour code. The perfume includes 21 fragrance ingredients which are listed below the graph on the left side. These ingredients are grouped in 12 odour families together with their olfactive contributions shown in the odour wheel on the right side. From the graph of the temporal evaporation profile the predominant odour families over time can be determined thereby establishing a prediction of the top note, core note and bottom note of perfume x.

Figure 5:
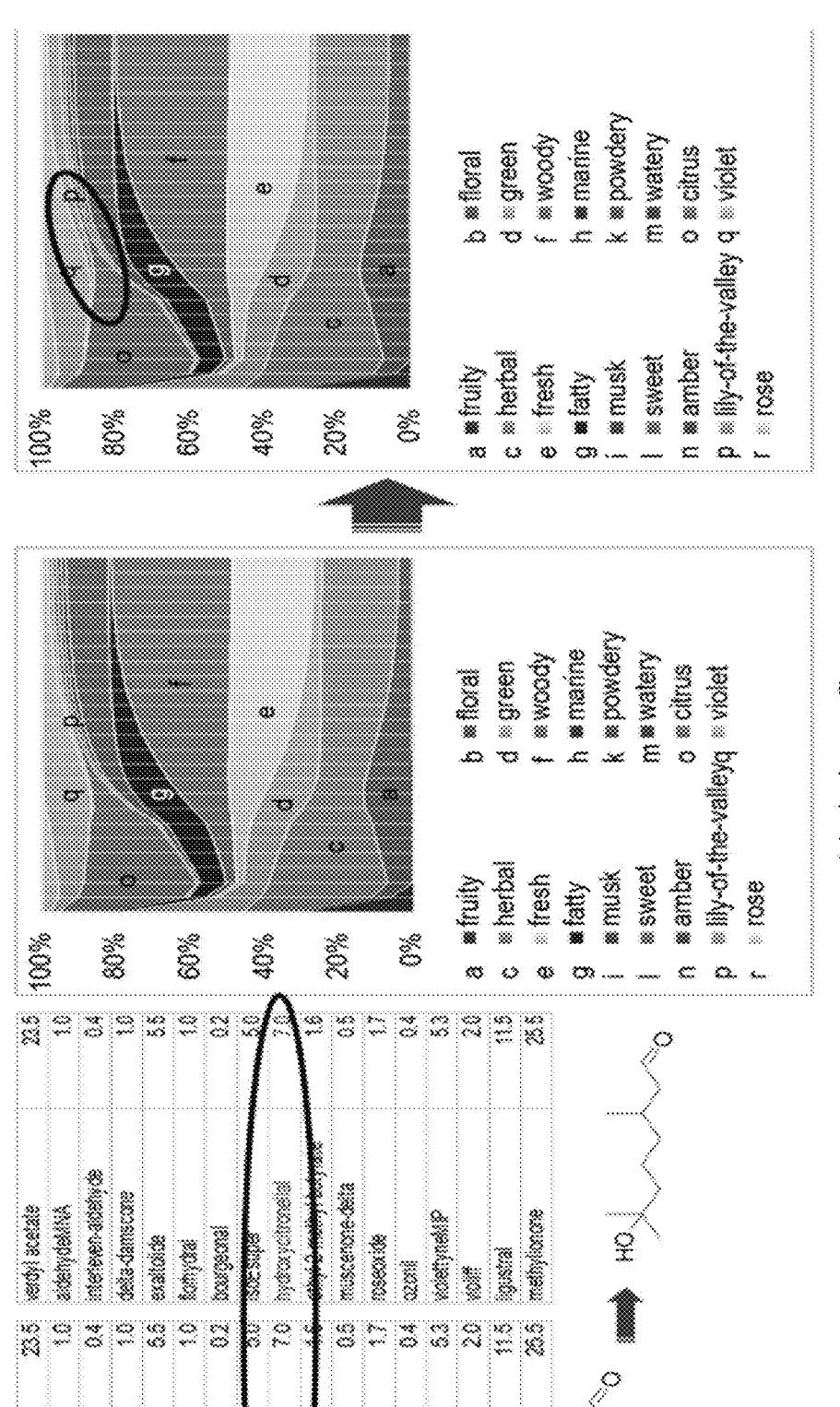
FIG. 5 shows the effect of exchanging one ingredient in a recipe of a perfume composition on the temporal evaporation profile predicted or generated by the method of the invention.

FIG. 5 shows the differences in the temporal evaporation profile of a fragrance composition when exchanging one ingredient with another. In the present case 7% lysmeral is exchanged for 7% hydroxycitronellal. No other amendment has been made to the recipe.

On the left side the temporal evaporation profile of the original recipe comprising lysmeral is shown whereas on the right side the temporal evaporation profile of the adapted recipe comprising hydroxycitronellal is shown. Both temporal evaporation profiles are shown as colour coded temporal odour families' profiles.

When comparing the two temporal evaporation profiles it can be seen that the biggest impact of the exchange to hydrocitronellal is the increase of the fractural amount of the lily-of-the-valley odour descriptions in a middle and late time interval, which indicates a slight shift in the core note and bottom note towards a pronounced floral (lily-of-the-valley) note of the adapted recipe.

Figure 6:
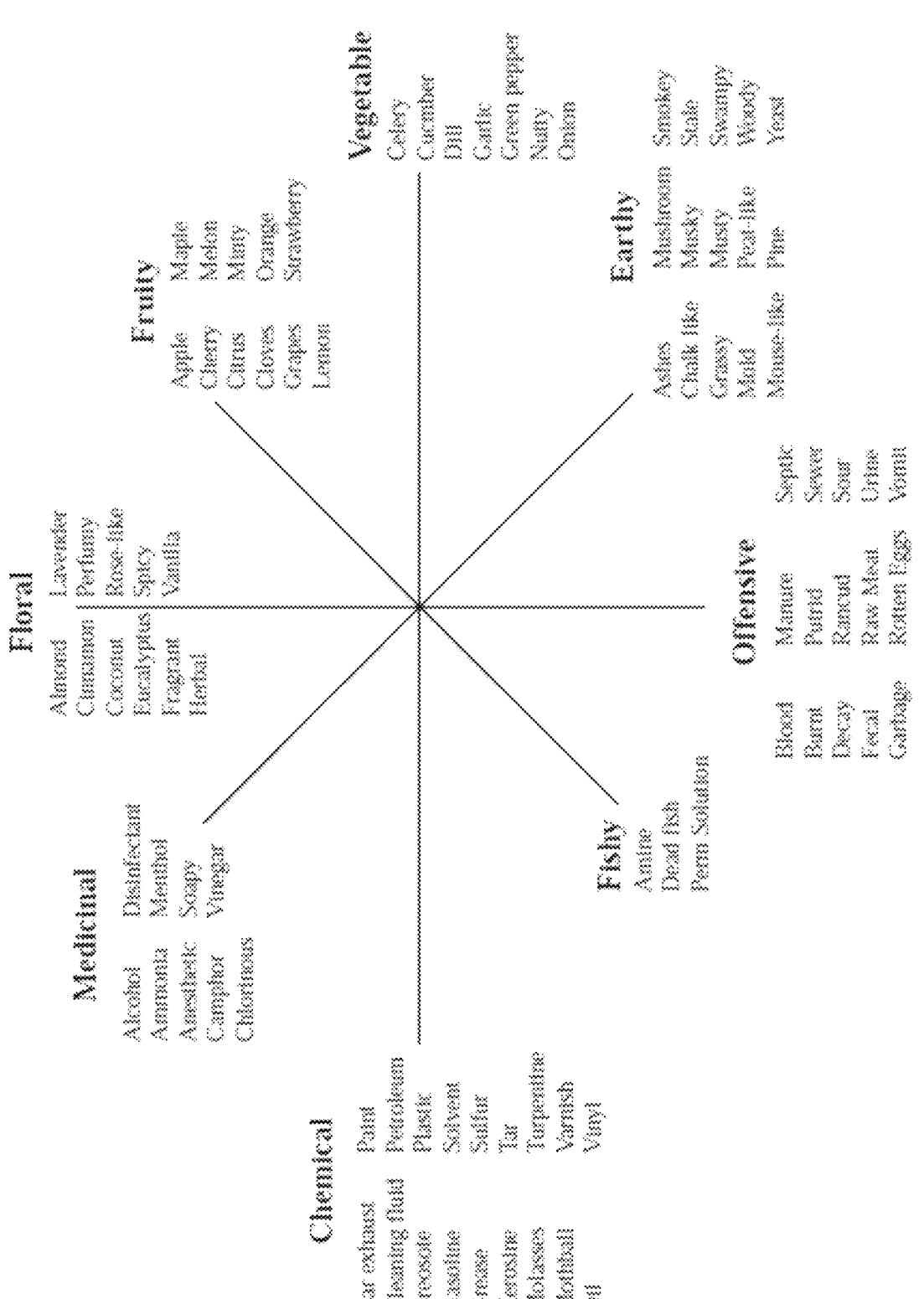
FIG. 6 shows the Odour Description Wheel, proposed by McGinley & McGinley (2002), Odor testing biosolids for decision-making.

FIG. 6 shows the Odour Description Wheel, proposed by McGinley & McGinley (2002), Odor testing biosolids for decision-making. In: Water Environment Federation Specialty Conference. Residuals and Biosolids Management Conference. Austin (EUA), 3-6 as one example of an odour description wheel showing odour description main and subclasses only for illustrating purposes. Said distinct odour description wheel is shown here as illustrative example as it only includes a limited number of main and subclasses but still gives an impression on how main and subclasses are selected.

Figure 7:
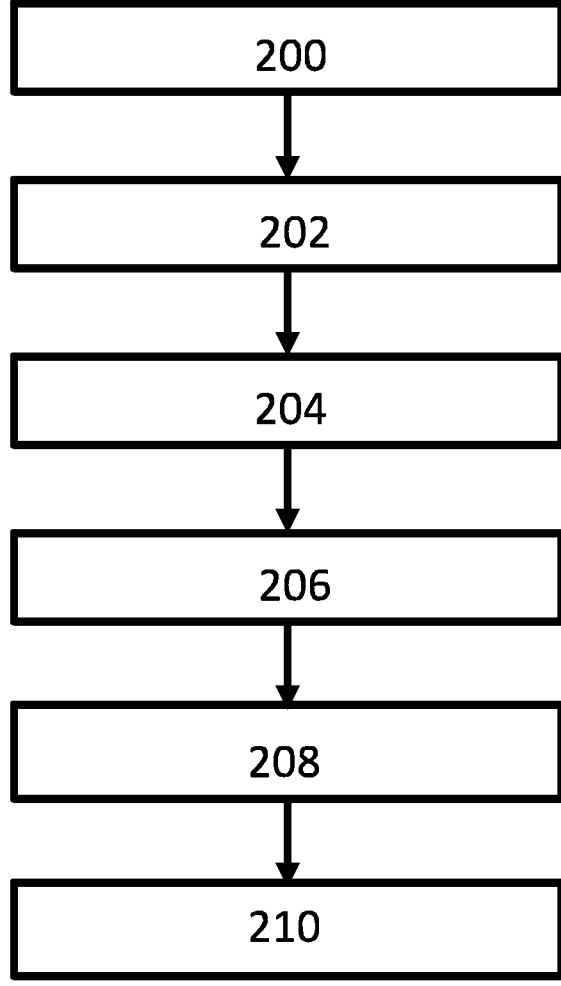
FIG. 7 shows an example of a flowchart for generating the temporal evaporation profile of a fragrance product.

FIG. 7 shows an example of a flowchart for generating the temporal evaporation profile of a fragrance product.

In a first step 200, fragrance composition data and matrix data are provided. The fragrance composition data may be associated with one or more fragrance ingredients of the fragrance composition. The fragrance composition data may include a fragrance ingredient identifier for each fragrance ingredient and an absolute or relative amount for each fragrance ingredient initially present in the composition. The fragrance ingredient identifier may include a representation of the molecule. The fragrance ingredient identifier may be associated with a representation of the molecular structure and/or the molecular geometry. This way the fragrance ingredient data may specify the composition of the fragrance composition. The matrix data may be associated with the matrix or the matrix material. The matrix data may include components identifiers associated with one or more matrix components.

In a second step 202, molecular geometry data related to one or more fragrance ingredient(s) may be provided. Such molecular geometry data may include a representation of the molecular geometry of the respective fragrance ingredient. The molecular geometry data may include a representation of the molecular geometry of the respective fragrance ingredient independent or dependent on the matrix data.

The molecular structure and/or molecular geometry data of the respective fragrance ingredient may be provided in form of a chemical file format specifying molecules. In particular the molecular structure and/or molecular geometry representation may specify atoms, bonds, coordinates and/or further property data associated with the molecule.

Chemical file formats may comprise computational data formats for coding chemical information. Examples are SMILES, XYZ, MDL, SDF or MOL as described below.

The Simplified Molecular Input Line Entry Specification (SMILES) may be a line notation for molecules. SMILES strings include connectivity but do not include 2D or 3D coordinates. The XYZ format is a simple format that usually gives the number of atoms in the first line, a comment on the second, followed by a number of lines with atomic symbols (or atomic numbers) and cartesian coordinates. The MDL number contains a unique identification number for each reaction and variation. The format is RXXXnnnnnnnn. R indicates a reaction, XXX indicates which database contains the reaction record. The numeric portion, nnnnnnnn, is an 8-digit number. SDF and MOL are other file formats from MDL Information Systems. The molfile consists of some header information, the Connection Table (CT) containing atom info, then bond connections and types, followed by sections for more complex information. "SDF" stands for structure-data file, and SDF files actually wrap the molfile format. Multiple compounds are delimited by lines consisting of four dollar signs ($$$$). A feature of the SDF format is its ability to include associated data such as e.g. molecular weight.

In a third step 204, vapor pressure data related to one or more fragrance ingredient(s) may be provided. Such vapor pressure data may include the vapour pressure associated with the respective fragrance ingredient. The vapour pressure may relate to the vapour pressure based on the molecular structure and/or geometry of the respective fragrance ingredient. The vapour pressure may relate to the vapour pressure based on the molecular structure and/or geometry of the respective fragrance ingredient independent of the matrix, dependent on the matrix or both.

In a fourth step 206, a time dependent activity coefficient may be determined for each fragrance ingredient in the condensed phase of the fragrance composition in the matrix over a predetermined period of time. Such time dependent activity coefficient may be determined based on the provided fragrance ingredients data and the matrix data.

The activity coefficient may link ideal behavior of the fragrance ingredient with real behavior the fragrance ingredient in condensed phase. The activity coefficient may thus include interactions between fragrance ingredient-fragrant ingredient and fragrant ingredient-matrix.

In addition to the interactions, changes in the fragrance composition (e.g. odorous oils) in the matrix over time e.g. due to different evaporation behavior of components, can be included by updating the composition in the gas and/or condensed phase and determining the activity coefficient for such updated composition. The activity coefficients of each fragrance ingredient in a given mixture at t0 and t1-tx may be calculated utilizing a quantum-chemical model, such as the conductor-like screening model for real solvents (COSMO-RS) that is based on chemical potentials in condensed phase of the fragrance composition in a matrix. Alternatively, these activity coefficients may be calculated based on a thermodynamic model, such as UNIQUAC, thereby utilizing group-contribution methods, such as UNI-FAQ.

The activity coefficients of every ingredient in the mixture may be calculated in the initially (t0). From the calculated vapor pressure and activity coefficient of each fragrant ingredient, the composition of the gas phase and the condensed phase of the fragrance composition is determined at the initial time t0. The activity coefficients may be updated in certain intervals over time (t1-tx) as the composition of the fragrance ingredients in the matrix of the condensed phase alters due to distinct evaporation of fragrant ingredients from the condensed phase into the gas phase. The activity coefficients hence allow to consider changes, as the mixture of the composition changes over time because of the distinct evaporation of the fragrance ingredients into the gas phase. Such a temporal altering of the condensed phase composition influences intermolecular interactions. This important fact is accounted for by updating the activity coefficients of every ingredient along the time axis. This is preferably done on-the-fly in the backend of the program.

In a fifth step 208, the temporal evaporation profile of the fragrance composition in the matrix is generated based on the vapour pressure data and the determined time-dependent activity coefficient. The temporal evaporation profile may relate to a time-dependent quantity associated with the evaporation behaviour of each fragrance ingredient of the fragrance product over the predetermined period of time. The temporal evaporation profile may relate to a time-dependent fractural amount of each fragrance ingredient in the gas phase and the condensed phase of the fragrance composition in the matrix over the predetermined period of time. In other words the temporal evaporation profile may indicate for each fragrance ingredient an absolute or relative amount of such ingredient in the condensed and in the gas phase. This way the fragrance product comprising the fragrance composition and the matrix material may be characterized through its dynamic evaporation characteristics. Such evaporation characteristics of the fragrance composition may correlate directly or indirectly to a performance characteristic of the fragrance product such as a performance characteristic.

In a sixth step 210, the generated temporal evaporation profile usable for validating the fragrance composition, the fragrance composition in the matrix or the fragrance product with respect to a performance characteristic is provided. The performance characteristic may relate to physical, chemical or physio-chemical characteristic. The performance characteristic may relate to an olfactory characteristic. The performance characteristic may comprise one or more physical, chemical or physio-chemical characteristic(s) directly or indirectly related to olfactory characteristic(s) of the fragrance product.

Figure 8:
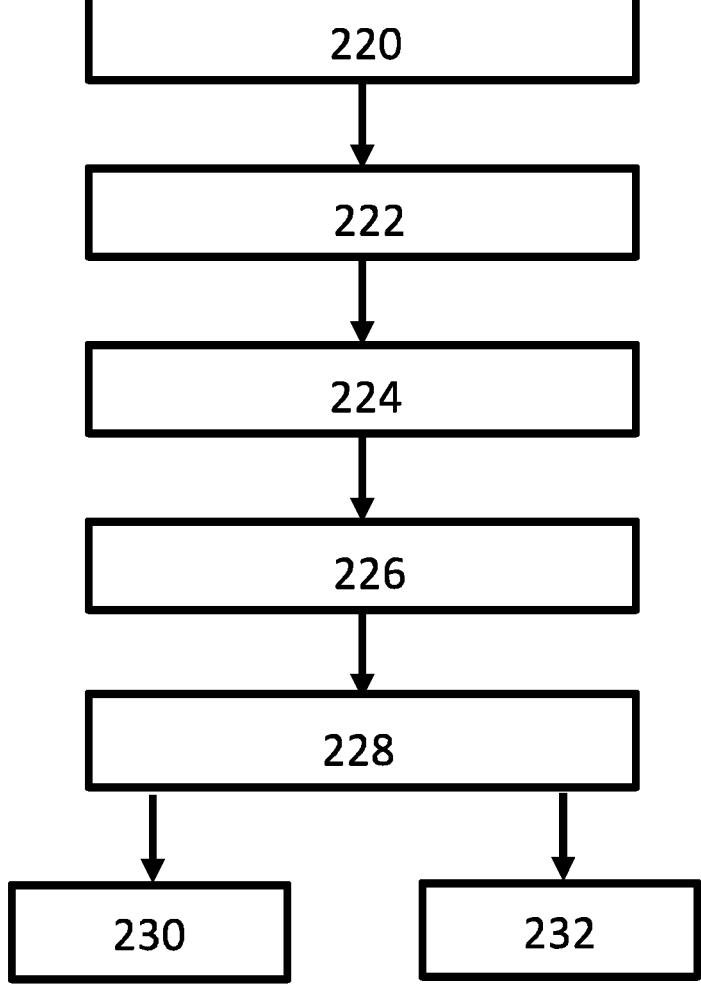
FIG. 8 shows an example of a flowchart for monitoring quality of the fragrance product in a production process of the fragrance product based on the temporal evaporation profile.

FIG. 8 shows an example of a flowchart for monitoring quality of the fragrance product in a production process of the fragrance product based on the temporal evaporation profile.

In a first step 220, the temporal evaporation profile as generated e.g. from the method of FIG. 7 is provided.

In a second step 222, the performance characteristic of the fragrance product is provided. The performance characteristic may be provided by or derived from measurement data. Such measurement data for instance includes measurement data provided by a chemical sensor. The chemical sensor may be at least partially selective with respect to different molecules. The chemical sensor may be configured to detect the presence of one or more molecule(s). The chemical sensor may be configured to detect the presence and absolute or relative amount one or more molecule(s). Chemical sensors are for instance based on electrochemical or optical sensing techniques to detect one or more molecules. Chemical sensors may detect molecules in the gas phase and/or in the condensed phase. As an example electrochemical sensors may be configured to detect a wide range of molecules. In addition their detection sensitivity may be tailored to specific molecules. As a further example infrared or photo detectors may be configured to detect a wide range of molecules. In addition their detection sensitivity may also be tailored to specific molecules. Chemical sensors may include a combination of one or more detection techniques to tailor the sensitivity of the sensor to the molecules to be detected.

In a third step 224, the performance characteristic as provided or measured may be compared to the evaporation profile as generated. In order to enable such comparison, the evaporation profile may include one or more physical, chemical or physio-chemical characteristic(s) that relate to the performance characteristic.

In one example the evaporation profile may specify the relative amount of a fragrance ingredient in the gas phase over time. In another example the evaporation profile may specify the relative amount of a fragrance ingredient in the condensed phase over time. In yet another example the evaporation profile may specify a substantivity, a tenacity, a bloom, a boost characteristic, a retention characteristic, a note, or a burning effectiveness of a fragrance product.

The performance characteristic may include data from a measurement over time of a fragrance product's gas and/or condensed phase. It may include the relative or absolute amount of one or more molecules in the gas and/or condensed phase over time. If the evaporation profile specifies the relative or absolute amount of one or more fragrance ingredient(s) in the gas and/or condensed phase over time, the measured values may be compared to the corresponding values provided via the evaporation profile.

In a fourth step 226, the temporal evaporation profile may be mapped to the performance characteristic. In other word the values corresponding to the performance characteristic may be determined from the temporal evaporation profile. In other embodiments the performance characteristic may be mapped to the temporal evaporation profile. Both options are equally applicable.

In a fifth step 228, the temporal evaporation profile and the performance characteristic or any corresponding values derived therefrom are used for validation. Such validation may be performed by comparing values or value ranges.

If the values lie within an acceptable range or value, such as a 1- or 2-standard deviation(s) interval, the fragrance product as measured may be valid in the sense that it fulfils the performance criterium or criteria. If the values do not lie within an acceptable range, such as a 1- or 2-standard deviation(s) interval, the fragrance product as measured may be invalid in the sense that it does not fulfil the performance criterium or criteria.

If the fragrance product is valid, e.g. a control signal for a production process may be triggered in step 230. Such control signal may be associated with the composition of the fragrance product. It may control dosing equipment for dosing of different components of the fragrance product in the production process.

If the fragrance product is invalid, e.g. a warning signal for the operator of the production process may be triggered in step 232. Such warning signal may signify the invalidity of the fragrance product. The invalidity may trigger a stop signal for the production process.

Figure 9:
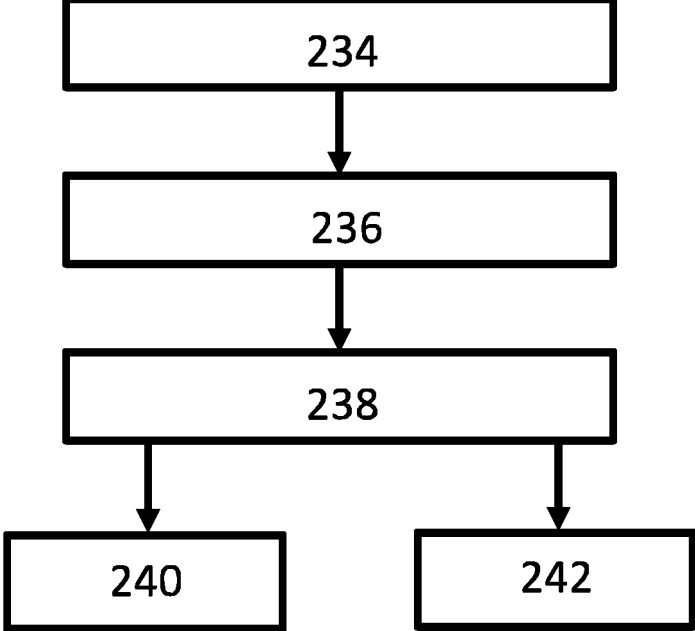
FIG. 9 shows an example of a flowchart for validating the production of the fragrance product with on at least one new matrix component or fragrance ingredient based on the temporal evaporation profile.

FIG. 9 shows an example of a flowchart for validating the production of the fragrance product with on at least one new matrix component or fragrance ingredient based on the temporal evaporation profile.

In a first step 234, an existing temporal evaporation profile as generated for the fragrance composition is provided, that has been produced from validated precursors.

In a first step 236, a new temporal evaporation profile is generated based on fragrance composition data that includes an ingredient identifier and related property data, which are associated with at least one new precursor. New precursors may include a new matrix component or a new fragrance ingredient.

In a first step 238, the existing and the new temporal evaporation profile are compared to validate the new precursor(s). If the comparison lies withing an acceptable range, the new precursor is valid. If the comparison does not lie withing an acceptable range, the new precursor is not valid.

If new precursor(s) is valid, e.g. a control signal for a production process based on the new precursor(s) may be triggered in step 240. Such control signal may by be associated with the composition of the fragrance product including the new precursor. It may control dosing equipment configured to dose different components of the fragrance product in the production process.

If the fragrance product is invalid, e.g. a warning signal for the operator of the production process may be triggered in step 242. Such warning signal may signify the invalidity of the new precursor(s). This may trigger a stop signal for the production process.

Figure 10:
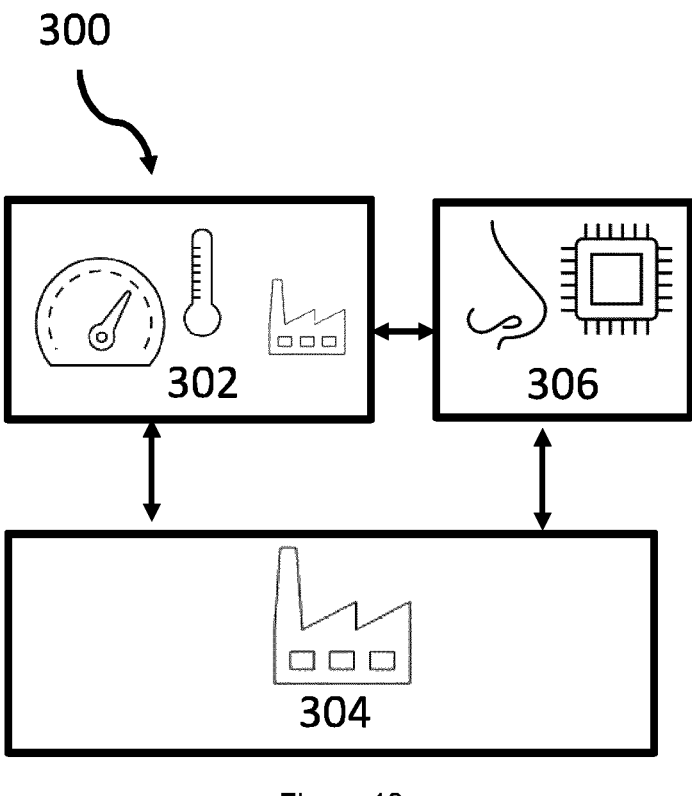
FIG. 10 shows an example of a production line for producing the fragrance product with a monitoring apparatus.

FIG. 10 shows an example of a production line 300 for producing the fragrance product with a monitoring apparatus 306.

The production line 300 may include dosing equipment 302 configured to dose different precursors of the fragrance product in the production process. The production line may include a conveyor system 304 to convey e.g. bottles, plastic packaging or other suitable packaging to be filled with the fragrance product. The production line may include a monitoring apparatus 306 configured to monitor quality of the fragrance product in a production process of the fragrance product based on the temporal evaporation profile as described in FIG. 8.

The monitoring apparatus 306 and/or the dosing equipment apparatus 302 may be configured to receive the temporal evaporation profile. The temporal evaporation profile may specify the composition data for the fragrance product including one or more fragrance ingredients and one or more matrix components. The temporal evaporation profile may include quality criteria like olfactory and/or physio-chemical properties. The monitoring apparatus may be configured to provide the composition data to the dosing equipment and vice versa. The dosing equipment may be configured to control the dosing based on the provided composition data.

The monitoring apparatus 306 may be configured to measure one or more performance characteristic(s). The monitoring apparatus 306 may be configured to compare the olfactory and physio-chemical properties, or any value derived from olfactory and physio-chemical properties to the measured performance characteristic(s). If the comparison lies within an acceptable range or value, the produced fragrant product fulfills quality criteria. If the comparison does not lie within an acceptable range or value, the produced fragrant product does not fulfill quality criteria. In the latter case the monitoring unit may be configured to notify an operator or to provide adjusted composition data to the dosing equipment 302.

Figure 11:
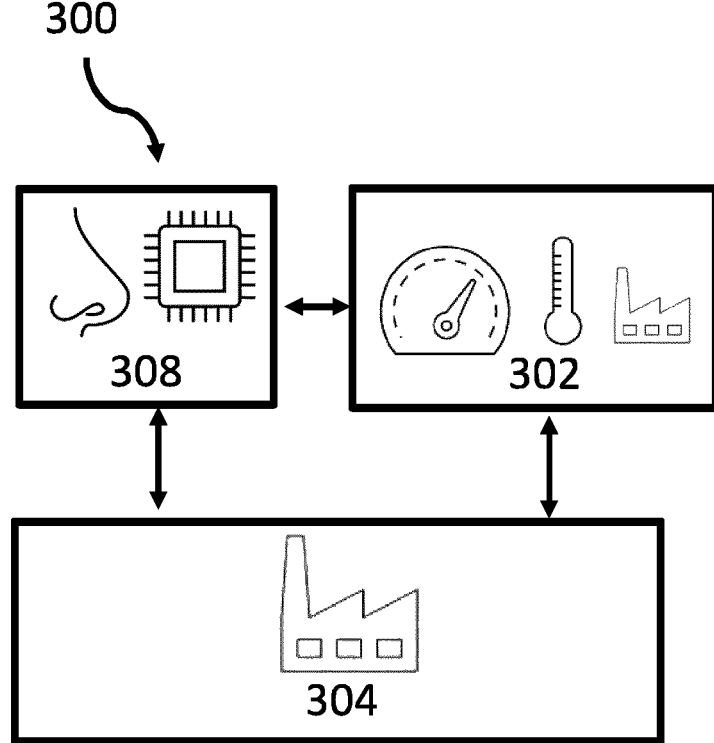
FIG. 11 shows an example of a production line for producing the fragrance product with a validation apparatus.

FIG. 11 shows another example of a production line 300 for producing the fragrance product with a validation apparatus 308.

The production line 300 may include dosing equipment 302 configured to dose different precursors of the fragrance product in the production process. The production line 300 may include a conveyor system 304 to convey e.g. bottles, plastic packaging or other suitable packaging to be filled with the fragrance product. The production line 300 may include a validation apparatus 308 configured to validate the production of the fragrance product with on at least one new matrix component or fragrance ingredient based on the temporal evaporation profile as described in the embodiment of FIG. 9.

The validation apparatus 308 may be configured to receive one or more data associated with the new precursor(s). The validation apparatus 308 may be configured to generate a new temporal evaporation profile based on the provided data related to the new precursor(s). The validation apparatus 308 may be configured to receive an existing temporal evaporation profile. The validation apparatus 308 may be configured to compare the existing and the new evaporation profile. The validation apparatus 308 may be configured to validate the new precursor(s) for production of the fragrance product based on such comparison. In addition, the validation apparatus 308 may be configured to validate the new precursor(s) for production of the fragrance product based on substrate evaporation profile generated for the fragrance product or fragrance composition on a matrix, such as a substrate like skin or wood. The validation apparatus 308 may be configured to compare the existing and substrate evaporation profile. This way not only the production of the fragrance product but also its application may be validated. The validation apparatus 308 may be configured to provide the composition data including the new precursor(s) to the dosing equipment and vice versa.

Combinations and modifications of the embodiments shown in FIGS. 8 and 9 are similarly possible. Both methods exemplify the strength of the methods described herein. The generation of the temporal evaporation profile of a fragrance product allow for objective assessment of the product in production, since the temporal evaporation profile can be compared to objective performance characteristics of the fragrance product. This allows for simplified and more reliable production through monitoring production of the fragrance product or through validating new precursor(s) to be used for producing the fragrance product.

In another exemplary embodiment of the present invention, a computer program or a computer program element is provided that is characterized by being adapted to execute the method steps of the method according to one of the preceding embodiments, on an appropriate system. The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above. According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

The invention claimed is:

1. A computer-implemented method for generating a temporal evaporation profile of a fragrance product for validating or monitoring production of the fragrance product, wherein the fragrance product comprises a fragrance composition and a matrix, and the fragrance composition comprises one or a plurality of fragrance ingredients, the method comprising:

a) receiving or obtaining fragrance composition data associated with one or more fragrance ingredients of the fragrance composition and matrix data associated with the matrix;

b) providing a vapour pressure of each fragrance ingredient based on the fragrance ingredients data;

c) determining, based on the fragrance ingredients data and the matrix data, a time-dependent interaction coefficient of each fragrance ingredient in a condensed phase of the fragrance composition in the matrix over a predetermined period of time;

d) generating, based on the provided vapour pressure and the determined time-dependent interaction coefficient, the temporal evaporation profile of the fragrance product, wherein the temporal evaporation profile is related to a time-dependent quantity associated with the evaporation behaviour of each fragrance ingredient of the fragrance product over the predetermined period of time; and e) validating or monitoring, based on the generated temporal evaporation profile, production of the fragrance product in the matrix with respect to a performance characteristic, wherein validating or monitoring production based on the generated temporal evaporation profile comprises comparing the temporal evaporation profile to a measured performance characteristic of the produced fragrance product to determine whether a quality criterion is fulfilled, and automatically transmitting to production-line equipment at least one of: (i) a control signal to dosing equipment to control or adjust dosing of one or more components of the fragrance product when the quality criterion is fulfilled, or (ii) a warning signal and/or a stop signal to a conveyor system when the quality criterion is not fulfilled.

2. The computer-implemented method according to claim 1, wherein the fragrance ingredients are grouped into a plurality of odour families in accordance with their olfactive contributions.

3. The computer-implemented method according to claim 1, wherein in step b), a vapour pressure is determined based on a molecular geometry representation of each fragrance ingredient using a quantum chemical model, wherein the molecular geometry representation is provided to determine vapor pressure for each fragrance ingredient.

4. The computer-implemented method according to claim 1, wherein a composition of a gas phase or the condensed phase, the interaction coefficient for each fragrance ingredient, the vapour pressure for each fragrance ingredient, or the time-dependent quantity associated with the evaporation behaviour for each fragrance ingredient is determined in a time dependent manner.

5. The computer-implemented method according to claim 1, wherein the temporal evaporation profile is used for monitoring quality of the fragrance product in a production process or for validating the production quality of the fragrance product based on at least one precursor or substrate.

6. The computer-implemented method according to claim 1, wherein in step e), the temporal evaporation profile is related to a time-dependent fractural amount of each fragrance ingredient in a gas phase or a condensed phase of the fragrance composition in the matrix over the predetermined period of time.

7. The computer-implemented method according to claim 1, wherein in step c) the vapour pressure of each fragrant ingredient is determined at a certain temperature, pressure and relative humidity using a chemical potential of each fragrant ingredient in a condensed phase and a gas phase.

8. The computer-implemented method according to claim 1, wherein in step e), the temporal evaporation profile is used for monitoring quality of the fragrance product in a production process or for validating the production of the fragrance product based on at least one precursor.

9. The computer-implemented method according to claim 1, wherein in step d), the determination of the time-dependent quantity associated with the evaporation behaviour or a time-dependent fractural amount of each fragrance ingredient in a gas phase of the fragrance composition in the matrix is adapted by including one or more of:

a diffusion parameter;

temperature dependence of an odorous experience;

an odor value;

a partition function in case of multiphase matrices; and explicit and component specific dipolar, dispersive and H-bonding interactions with their environment.

10. A computer-implemented method for monitoring production of a fragrance product, the method comprising:

receiving the temporal evaporation profile as generated according to claim 1, wherein the temporal evaporation profile is indicative of quality criteria, measuring, by a sensor, a performance characteristic of the produced fragrance product, determining, based on the temporal evaporation profile and the performance characteristic, if the produced fragrance product fulfils quality criteria; and responsive to the determination:

when the quality criteria are fulfilled, automatically transmitting a control signal to dosing equipment of a production line to continue dosing according to composition data; or when the quality criteria are not fulfilled, automatically transmitting at least one of a control signal to adjust dosing of one or more components and a stop signal to a conveyor system.

11. An apparatus for monitoring production of a fragrance product, the apparatus comprising one or more processing units configured to monitor production, wherein the processing units include instructions, which when executed on the one or more processing units perform the method claim 10.

12. A computer-implemented method for validating production of a fragrance product, the method comprising:

receiving an existing temporal evaporation profile as generated according to claim 1 based on existing fragrance data associated with existing fragrance ingredients and matrix data associated with existing matrix components, wherein the temporal evaporation profile is indicative of quality criteria, receiving precursor data of at least one precursor and generating a temporal evaporation profile according to claim 1 based on the precursor data, determining, based on the existing temporal evaporation profile and the new temporal evaporation profile, if the at least one precursor fulfils quality criteria, and responsive to the determination:

when the at least one precursor fulfills the quality criteria, automatically transmitting a control signal to dosing equipment of a production line to dose the precursor(s); or when the precursor(s) does not fulfill the quality criteria, automatically transmitting a warning signal and/or a stop signal to a conveyor system.

13. An apparatus for validating production of a fragrance product, the apparatus comprising one or more processing units configured to validate production of a fragrance product, wherein the processing units include instructions, which when executed on the one or more processing units perform the method of claim 12.

14. An apparatus for generating a temporal evaporation profile of a fragrance product for validating or monitoring production of the fragrance product, wherein the apparatus comprises a fragrance composition and a matrix, and the fragrance composition comprises one or a plurality of fragrance ingredients, the apparatus comprising one or more processing units configured to generate a temporal evaporation profile of a fragrance product, wherein the processing units include instructions, which when executed on the one or more processing units perform the method of claim 1.

15. A non-transitory computer-readable medium comprising instructions, which when executed by a processing unit, cause the processing unit to carry out the method of claim 1.

* * * * *